United States Patent
Alcalde-Pais et al.

(10) Patent No.: US 9,493,434 B2
(45) Date of Patent: Nov. 15, 2016

(54) SUBSTITUTED INDENES AS MEDICAMENTS

(71) Applicant: LABORATORIOS DEL DR. ESTEVE S.A., Barcelona (ES)

(72) Inventors: Maria de las Ermitas Alcalde-Pais, Sant Just Desvern (ES); Carmen Almansa-Rosales, Barcelona (ES); José Luis Diaz Fernández, Manresa (ES); María de les Neus Mesquida-Estevez, Sant Esteve Sesrovires (ES); Laura Paloma-Romeu, La Garriga (ES)

(73) Assignee: LABORATORIOS DEL DR. ESTEVE S.A., Barcelona (ES)

( * ) Notice: Subject to any disclaimer, the term of this patent is extended or adjusted under 35 U.S.C. 154(b) by 0 days.

(21) Appl. No.: 14/412,021

(22) PCT Filed: Jul. 3, 2013

(86) PCT No.: PCT/EP2013/063989
§ 371 (c)(1),
(2) Date: Dec. 30, 2014

(87) PCT Pub. No.: WO2014/006071
PCT Pub. Date: Jan. 9, 2014

(65) Prior Publication Data
US 2015/0158831 A1 Jun. 11, 2015

(30) Foreign Application Priority Data
Jul. 3, 2012 (EP) ..................... 12382268

(51) Int. Cl.
| | |
|---|---|
| A61K 31/137 | (2006.01) |
| C07C 211/34 | (2006.01) |
| C07D 295/03 | (2006.01) |
| C07D 231/12 | (2006.01) |
| C07D 333/20 | (2006.01) |
| C07D 239/26 | (2006.01) |
| C07D 249/06 | (2006.01) |
| C07D 261/08 | (2006.01) |
| C07D 213/36 | (2006.01) |
| C07D 295/073 | (2006.01) |
| C07D 295/096 | (2006.01) |

(52) U.S. Cl.
CPC ........... *C07D 295/03* (2013.01); *C07D 213/36* (2013.01); *C07D 231/12* (2013.01); *C07D 239/26* (2013.01); *C07D 249/06* (2013.01); *C07D 261/08* (2013.01); *C07D 295/073* (2013.01); *C07D 295/096* (2013.01); *C07D 333/20* (2013.01)

(58) Field of Classification Search
CPC .................... A61K 31/137; C07C 211/34
USPC ........ 514/657; 540/484, 575; 544/106, 242, 544/403; 546/205, 348; 548/247, 255, 548/373.1; 549/80; 564/428; 585/400
See application file for complete search history.

(56) References Cited

FOREIGN PATENT DOCUMENTS

| EP | 1634873 | 3/2006 |
|---|---|---|
| EP | 2682391 | * 1/2014 |
| WO | WO 2007/054257 | 5/2007 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Wolff, Manfred E., Ed. Burger's Medicinal Chemistry and Drug Discovery—Fifth Edition, vol. 1: Principles and Practice, New York: John Wiley & Sons, 1994, 975-977.*
Hackam, et al. JAMA, 296(14), 2006, 1731-1732.*
Berardi, et al., Journal Med. Chem. vol. 41, p. 3940-3947, 1998.
Bowen, Pharmaceutica Acta Helvetiae, vol. 74, p. 211-218, 2000.
Chordia, et al., Jour. Med. Chem., vol. 48, p. 5131-5139, 2005.
Dehaven-Hudkins, et al., European Journal of Pharmacology—Molecular Pharmacology Section vol. 227, p. 371-378, 1992.
Hanner, et al., Proc. Natl. Acad. Sci. USA, vol. 93, p. 8072-8077, Jul. 1996.
International Search Report for PCT/EP2013/003989 of Oct. 16, 2013.
Jiang, et al., Organic Letters, vol. 12, No. 2, p. 228-231, 2010.
Kaiser, et al., Neurotransmissions, vol. 7, No. 1, p. 1-5, 1991.
Merskey, et al., Classification of Chronic Pain Second Edition, p. 210-213, 2002.
Quirion, et al., Tips, vol. 13, p. 85-86, Mar. 1992.
Ronsisvalle, et al., Pure Appl. Chem., vol. 73, No. 9, p. 1499-1509, 2001.
Snyder, et al., Journal of Neuropsychiatry, vol. 1, No. 1, p. 7-15, Winter 1998.

(Continued)

*Primary Examiner* — Douglas M Willis
(74) *Attorney, Agent, or Firm* — Hueschen and Sage

(57) ABSTRACT

The present invention relates to new indene derivatives of formula (I)

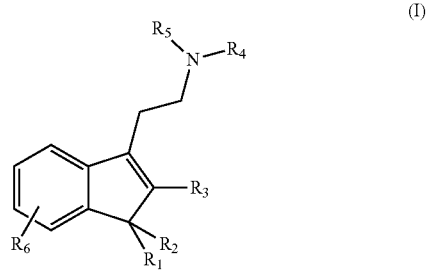

having a great affinity for sigma receptors, especially sigma-1 receptors, as well as to the process for the preparation thereof, to compositions comprising them, and to their use as medicaments.

9 Claims, No Drawings

(56) References Cited

OTHER PUBLICATIONS

Walker, et al., Pharmacological Review, vol. 42, No. 4, p. 355-402.
Bermack, et al., International Journal of Neuropsychopharmacology, 2002, 5, 53-62.
Bermack, et al., Journal of Pharmacology and Experimental Therapeutics, 2004, 310, 578-583.
Berthois, et al., British Journal of Cancer, 2003, 88, 438-446.
Bourrié, et al., European Journal of Pharmacology, 2002, 456, 123-131.
Cendán, et al., European Journal of Pharmacology, 2005, 511, 73-74.
Cendán, et al., Psychopharmacology, 2005, 182, 485-493.
Chaki, et al,. Journal of Pharmacology and Experimental Therapeutics, 2003, 304, 818-826.
Chien, at al., European Journal of Pharmacology, 1993, 250, R7-R8.
Chien, et al., European Journal of Pharmacology, 1995, 294, 303-308.
Chien, et al., Journal of Pharmacology and Experimental Therapeutics, 1994, 271, 1583-1590.
Goyagi, et al., Stroke, 2001, 32, 1613-1620.
Harukuni, et al., Stroke, 2000, 31, 976-882.
John, et al., Cancer Research, 1995, 55, 3022-3027.
John, et al., Cancer Research, 1999, 59, 4578-4583.
Matsumoto, et al., European Journal of Pharmacology, 2003, 469, 1-12.
Maurice, et al., British Journal of Pharmacology, 2001, 134, 1731-1741.
Maurice, et al., Neuroscience and Biobehavioral Reviews, 2002, 26, 499-527.
Maurice, et al., Pharmacology, Biochemistry and Behavior, 2003, 74, 869-876.
Maurice, et al., Pharmacopsychiatry, 2004, 37 Suppl 3, S198-S207.
Mei, et al., Journal of Pharmacology and Experimental Therapeutics, 2002, 300, 1070-1074.
Ovalle, et al., European Journal of Neuroscience, 2001, 13, 909-915.
Renaudo, et al., Journal of Pharmacology and Experimental Therapeutics, 2004, 311, 1105-1114.
Romieu, et al., Journal of Neuroscience, 2003, 23, 3572-3576.
Romieu, et al., Neuropsychopharmacology, 2002, 26, 444-455.
Roth, et al., Journal of Leukocyte Biology, 2005, 78, 1198-1203.
Simony-Lafontaine, et al., British Journal of Cancer, 2000, 82, 1958-1966.
Skuza, et al, Pharmacopsychiatry, 2004, 37, Suppl. 3, S183-188.
Smith, et al., Investigative Ophthalmology & Visual Science, 2008, 49, 4154-4161.
Spruce, et al., Cancer Research, 2004, 64, 4875-4886.
Urani, et al., Journal of Pharmacology and Experimental Therapeutics, 2001, 298, 1269-1279.
Vilner, et al., Cancer Research, 1995, 55, 408-413.
Zhu, et al., Journal of Immunology, 2003, 170, 3585-3591.

\* cited by examiner

SUBSTITUTED INDENES AS MEDICAMENTS

FIELD OF THE INVENTION

The present invention relates to new indene derivatives having a great affinity for sigma receptors, especially sigma-1 receptors, as well as to the process for the preparation thereof, to compositions comprising them, and to their use as medicaments.

BACKGROUND OF THE INVENTION

The search for new therapeutic agents has been greatly aided in recent years by better understanding of the structure of proteins and other biomolecules associated with target diseases. One important class of these proteins are the sigma (σ) receptors, cell surface receptors of the central nervous system (CNS) which may be related to the dysphoric, hallucinogenic and cardiac stimulant effects of opioids. From studies of the biology and function of sigma receptors, evidence has been presented that sigma receptor ligands may be useful in the treatment of psychosis and movement disorders such as dystonia and tardive dyskinesia, and motor disturbances associated with Huntington's chorea or Tourette's syndrome and in Parkinson's disease (Walker, J. M. et al, Pharmacological Reviews, 1990, 42, 355). It has been reported that the known sigma receptor ligand rimcazole clinically shows effects in the treatment of psychosis (Snyder, S. H., Largent, B. L. J. Neuropsychiatry 1989, 1, 7). The sigma binding sites have preferential affinity for the dextrorotatory isomers of certain opiate benzomorphans, such as (+)-SKF-10047, (+)-cyclazocine, and (+)-pentazocine and also for some narcoleptics such as haloperidol.

"The sigma receptor/s" as used in this application is/are well known and defined using the following citation: This binding site represents a typical protein different from opioid, NMDA, dopaminergic, and other known neurotransmitter or hormone receptor families (G. Ronsisvalle et al. Pure Appl. Chem. 73, 1499-1509 (2001)).

The sigma receptor has at least two subtypes, which may be discriminated by stereoselective isomers of these pharmacoactive drugs. SKF-10047 has nanomolar affinity for the sigma 1 (σ-1) site, and has micromolar affinity for the sigma 2 (σ-2) site. Haloperidol has similar affinities for both subtypes.

The Sigma-1 receptor is a non-opiaceous type receptor expressed in numerous adult mammal tissues (e.g. central nervous system, ovary, testicle, placenta, adrenal gland, spleen, liver, kidney, gastrointestinal tract) as well as in embryo development from its earliest stages, and is apparently involved in a large number of physiological functions. Its high affinity for various pharmaceuticals has been described, such as for SKF-10047, (+)-pentazocine, haloperidol and rimcazole, among others, known ligands with analgesic, anxiolytic, antidepressive, antiamnesic, antipsychotic and neuroprotective activity. The sigma-1 receptor is of great interest in pharmacology in view of its possible physiological role in processes related to analgesia, anxiety, addiction, amnesia, depression, schizophrenia, stress, neuroprotection and psychosis [Kaiser et al (1991) Neurotransmissions 7 (1): 1-5], [Walker, J. M. et al, Pharmacological Reviews, 1990, 42, 355] and [Bowen W. D. (2000) Pharmaceutica Acta Helvetiae 74: 211-218].

The Sigma-2 receptor is also expressed in numerous adult mammal tissues (e.g. nervous system, immune system, endocrine system, liver, kidney). Sigma-2 receptors can be components in a new apoptosis route that may play an important role in regulating cell proliferation or in cell development. This route seems to consist of Sigma-2 receptors joined to intracellular membranes, located in organelles storing calcium, such as the endoplasmic reticulum and mitochondria, which also have the ability to release calcium from these organelles. The calcium signals can be used in the signaling route for normal cells and/or in induction of apoptosis.

Agonists of Sigma-2 receptors induce changes in cell morphology, apoptosis in several types of cell lines and regulate the expression of p-glycoprotein mRNA, so that they are potentially useful as antineoplasic agents for treatment of cancer. In fact, Sigma-2 receptor agonists have been observed to induce apoptosis in mammary tumour cell lines resistant to common antineoplasic agents that damage DNA. In addition, agonists of Sigma-2 receptors enhance the cytotoxic effects of these antineoplasic agents at concentrations in which the agonist is not cytotoxic. Thus, agonists of Sigma-2 receptors can be used as antineoplasic agents at doses inducing apoptosis or at sub-toxic doses in combination with other antineoplasic agents to revert the resistance to the drug, thereby allowing using lower doses of the antineoplasic agent and considerably reducing its adverse effects.

Antagonists of Sigma-2 receptors can prevent the irreversible motor side effects caused by typical neuroleptic agents. In fact, it has been found that antagonists of Sigma-2 receptors can be useful as agents for improving the weakening effects of delayed dyskinesia appearing in patients due to chronic treatment of psychosis with typical antipsychotic drugs, such as haloperidol. Sigma-2 receptors also seem to play a role in certain degenerative disorders in which blocking these receptors could be useful.

Endogenous sigma ligands are not known, although progesterone has been suggested to be one of them. Possible sigma-site-mediated drug effects include modulation of glutamate receptor function, neurotransmitter response, neuroprotection, behavior, and cognition (Quirion, R. et al. Trends Pharmacol. Sci., 1992, 13:85-86). Most studies have implied that sigma binding sites (receptors) are plasmalemmal elements of the signal transduction cascade. Drugs reported to be selective sigma ligands have been evaluated as antipsychotics (Hanner, M. et al. Proc. Natl. Acad. Sci., 1996, 93:8072-8077). The existence of sigma receptors in the CNS, immune and endocrine systems have suggested a likelihood that it may serve as link between the three systems.

In view of the potential therapeutic applications of agonists or antagonists of the sigma receptor, a great effort has been directed to find selective ligands. Different sigma receptor ligands have been reported.

For instance, the international patent application WO2007/098961 describes 4,5,6,7 tetrahydrobenzo[b]thiophene derivatives having pharmacological activity towards the sigma receptor.

Spiro[benzopyran] or spiro[benzofuran] derivatives were also disclosed in EP1847542 as well as pyrazole derivatives (EP1634873) with pharmacological activity on sigma receptors.

WO2009071657 also reports tricyclic triazolic compounds having good activity towards sigma receptors.

Some indene derivatives with therapeutic activity have been disclosed in the prior art, for instance U.S. Pat. Nos. 5,092,827, 6,025,394, 5,958,982, 5,965,619, 6,028,116, US 2001/0006965 and US 2001/0020020 describe indene derivatives as being suitable for treating psoriasis, acne, sarcoidosis, pre-cancerous lesions and neoplasias, as well as diabetic retinopathy and macular degeneration. The therapeutic effect of these compounds seems to originate in their inhibitive action on a specific phosphodiesterase of cGMP (cGMP PDE), as described in the U.S. Pat. No. 6,177,471. None of these references discloses the indene derivatives of the present invention. In addition none of these references suggest that indene derivatives can be active towards sigma receptors.

WO2007054257 also reports indene derivatives with therapeutic activity, namely activity towards 5-HT6 receptors. These indenes are however different from the ones of the present invention as they are always substituted with a sulphonamido group in the benzene ring of the indene moiety.

Nevertheless, there is still a need to find compounds having pharmacological activity towards the sigma receptor, being both effective and selective, and having good "drugability" properties, i.e. good pharmaceutical properties related to administration, distribution, metabolism and excretion.

SUMMARY OF THE INVENTION

The present invention discloses novel compounds with great affinity to sigma receptors which might be used for the treatment of sigma related disorders or diseases.

Specifically, it is an object of the present invention novel indene derivatives of general formula (I):

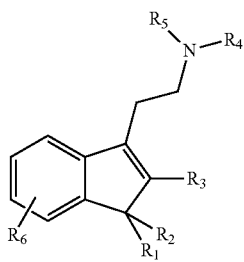

(I)

Another object of the invention is the different processes for preparation of compounds of general formula (I).

Another object of the invention refers to the use of such compounds of general formula (I) for the treatment or prophylaxis of sigma receptor mediated diseases or conditions, especially sigma-1 mediated diseases or conditions. Within the group of diseases or conditions mediated by the sigma receptor for which the compounds of the invention are effective, diarrhea, lipoprotein disorders, hyperlipidemia, hypertriglyceridemia, hypercholesterolemia, obesity, migraine, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer, psychotic conditions, in particular depression, anxiety or schizophrenia; inflammation or autoimmune diseases, may be cited. Compounds of the invention are very good and are especially effective for the treatment and prophylaxis of pain, especially neuropathic pain, inflammatory pain or other pain conditions involving allodynia and/or hyperalgesia.

It is also an object of the invention pharmaceutical compositions comprising one or more compounds of general formula (I) with at least one pharmaceutically acceptable excipient. The pharmaceutical compositions in accordance with the invention can be adapted in order to be administered by any route of administration, be it orally or parenterally, such as pulmonarily, nasally, rectally and/or intravenously. Therefore, the formulation in accordance with the invention may be adapted for topical or systemic application, particularly for dermal, subcutaneous, intramuscular, intra-articular, intraperitoneal, pulmonary, buccal, sublingual, nasal, percutaneous, vaginal, oral or parenteral application.

DETAILED DESCRIPTION OF THE INVENTION

The invention first relates to a compound of general formula (I):

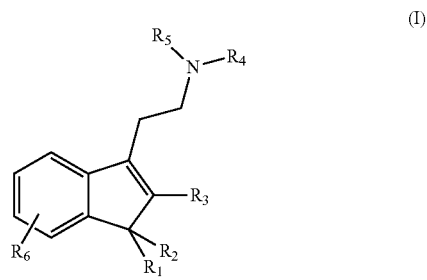

(I)

where $R_1$, $R_2$ and $R_3$ are independently selected from hydrogen or a branched or unbranched, saturated or unsaturated, optionally at least mono-substituted, aliphatic radical $C_{1-10}$, with the proviso that $R_1$ and $R_2$ are always identical;

$R_4$ and $R_5$ together with the bridging nitrogen form a $C_{3-9}$ heterocycloalkyl, optionally containing at least one additional heteroatom as ring member and optionally substituted by a branched or unbranched, saturated or unsaturated aliphatic radical $C_{1-10}$ or by an aryl group optionally monosubstituted by a $C_{1-6}$ alkyl or a halogen;

$R_6$ is a 5- or 6-membered aryl or heteroaryl radical optionally mono- or polysubstituted by substituents independently selected from a $C_{1-6}$ alkyl group, a linear or branched $C_{1-6}$ alkoxy group, an optionally at least monosubstituted phenyl group, —F, —Cl, —I, —Br, —CF$_3$, —CH$_2$F, —CHF$_2$, —CN, —OH, —SH, —NH$_2$, oxo, —(C═O)R', —SR', —SOR', —SO$_2$R', —N(C═O) OR', —NHR', —NR'R" whereby R' and optionally R" for each substitutent independently represents a linear or branched $C_{1-6}$-alkyl group;

or a pharmaceutically acceptable salt, isomer, prodrug or solvate thereof.

"Halogen" or "halo" as referred in the present invention represent fluorine, chlorine, bromine or iodine.

"Aliphatic radicals $C_{1-10}$", as referred to in the present invention, are optionally mono- or polysubstituted and may be branched or unbranched, saturated or unsaturated. Unsaturated aliphatic groups, as defined in the present invention, include alkyl, alkenyl and alkinyl radicals. Preferred aliphatic radicals according to the present invention include but are not restricted to methyl, ethyl, vinyl (ethenyl), ethinyl, propyl, n-propyl, isopropyl, allyl (2-propenyl), 1-propinyl, methylethyl, butyl, n-butyl, iso-butyl, sec-butyl, tert-butyl butenyl, butinyl, 1-methylpropyl, 2-methylpropyl, 1,1-dimethylethyl, pentyl, n-pentyl, isopentyl, 1,1-dimethylpropyl, 1,2-dimethylpropyl, 2,2-dimethylpropyl, hexyl, 1-methylpentyl, n-heptyl, n-octyl, n-nonyl and n-decyl. Preferred substituents for aliphatic radicals, according to the present invention, are a $C_{1-6}$ alkyl group, cycloalkyl $C_{3-9}$ group, a linear or branched $C_{1-6}$ alkoxy group, —F, —Cl, —I, —Br, —CF$_3$, —CH$_2$F, —CHF$_2$, —CN, —OH, —SH, —NH$_2$, oxo, —(C═O)R', —SR', —SOR', —SO$_2$R', —NHR', —NR'R" whereby R' and optionally R" for each substitutent independently represents a linear or branched $C_{1-6}$-alkyl group.

"Alkyl radicals", as referred to in the present invention, are saturated aliphatic radicals. They may be linear or branched and are optionally substituted. $C_{1-6}$ alkyl as expressed in the present invention means an alkyl radical of 1, 2, 3, 4, 5 or 6 carbon atoms.

"Cycloalkyl radical $C_{3-9}$", as referred to in the present invention, are understood as meaning saturated, cyclic hydrocarbons, which can optionally be unsubstituted, mono- or polysubstituted. In these radicals, for example $C_{3-4}$-cycloalkyl represents C3- or C4-cycloalkyl, $C_{3-5}$-cycloalkyl represents C3-, C4- or C5-cycloalkyl, etc. Cycloalkyl radical as referred in the present invention may optionally contain at least one unsaturation but they cannot be aromatic cycles. Examples for cycloalkyl radical preferably include but are not restricted to cyclopropyl, 2-methylcyclopropyl, cyclopropylmethyl, cyclobutyl, cyclopentyl, cyclopentylmethyl, cyclohexyl, cycloheptyl, cyclooctyl, acetyl, tert-butyl, adamantyl, noradamantyl, pyrroline, pyrrolidine, pyrrolidineone, pyrazoline, pyrazolinone, oxopyrazolinone, aziridine, azetidine, tetrahydropyrrole, oxirane, oxetane, dioxetane, tetrahydropyrane, tetrahydrofurane, tetrahydro-2H-thiopyran, dioxane, dioxolane, oxathiolane, oxazolidine, thiirane, thietane, thiolane, thiane, thiazolidine, pyrazine piperidine, piperazine, morpholine, azepane or diazepane. Cycloalkyl radicals $C_{3-9}$, as defined in the present invention, are optionally mono- or polysubstituted by substitutents independently selected from a $C_{1-6}$ alkyl group, a linear or branched $C_{1-6}$ alkoxy group, —F, —Cl, —I, —Br, —CF$_3$, —CH$_2$F, —CHF$_2$, —CN, —OH, —SH, —NH$_2$, oxo, —(C═O)R', —SR', —SOR', —SO$_2$R', —NHR', —NR'R" whereby R' and optionally R" for each substituent independently represents a linear or branched $C_{1-6}$-alkyl group.

"Heterocycloalkyl" as referred to in the present invention, are understood as meaning saturated, cyclic hydrocarbons having from 3 to 9 carbon atoms which can optionally be unsubstituted, mono- or polysubstituted and which have at least one heteroatom in their structure selected from S, N or O. Heterocycloalkyl radical as referred in the present invention may optionally contain at least one unsaturation but they cannot be aromatic cycles. Examples for heterocycloalkyl radical preferably include but are not restricted to pyrroline, pyrrolidine, pyrazoline, aziridine, azetidine, tetrahydropyrrole, oxirane, oxetane, dioxetane, tetrahydropyrane, tetrahydrofurane, tetrahydro-2H-thiopyran, dioxane, dioxolane, oxathiolane, oxazolidine, thietane, thiolane, thiane, thiazolidine, piperidine, piperazine, morpholine, azepane or diazepane. Heterocycloalkyl radicals, as defined in the present invention, are optionally mono- or polysubstituted by substitutents independently selected from $C_{1-6}$ alkyl group, a linear or branched $C_{1-6}$ alkoxy group, —F, —Cl, —I, —Br, —CF$_3$, —CH$_2$F, —CHF$_2$, —CN, —OH, —SH, —NH$_2$, oxo, —(C═O)R', —SR', —SOR', —SO$_2$R', —NHR', —NR'R" whereby R' and optionally R" for each substitutent independently represents a linear or branched $C_{1-6}$-alkyl group.

An "aryl radical", as referred to in the present invention, is understood as meaning ring systems with at least one aromatic ring but without heteroatoms even in only one of the rings. These aryl radicals may optionally be mono- or polysubstituted by substitutents independently selected from a $C_{1-6}$ alkyl group, a linear or branched $C_{1-6}$ alkoxy group, an optionally at least mono-substituted phenyl group, —F, —Cl, —I, —Br, —CF$_3$, —CH$_2$F, —CHF$_2$, —CN, —OH, —SH, —NH$_2$, oxo, —(C═O)R', —SR', —SOR', —SO$_2$R', —N(C═O) OR', —NHR', —NR'R" whereby R' and optionally R" for each substitutent independently represents a linear or branched $C_{1-6}$-alkyl group. Preferred examples of aryl radicals include but are not restricted to phenyl, naphthyl, fluoranthenyl, fluorenyl, tetralinyl or indanyl or anthracenyl radicals, which may optionally be mono- or polysubstituted, if not defined otherwise.

A "heteroaryl radical", is understood as meaning heterocyclic ring systems which have at least one aromatic ring and may optionally contain one or more heteroatoms from the group consisting of nitrogen, oxygen and/or sulfur and may optionally be mono- or polysubstituted by substitutents independently selected from a $C_{1-6}$ alkyl group, a linear or branched $C_{1-6}$ alkoxy group, F, Cl, I, Br, CF$_3$, CH$_2$F, CHF$_2$, CN, OH, SH, NH$_2$, oxo, (C═O)R', SR', SOR', SO$_2$R', NHR', NR'R" whereby R' and optionally R" for each substitutent independently represents a linear or branched $C_{1-6}$ alkyl group. Preferred examples of heteroaryls include but are not restricted to furan, benzofuran, thiophene, benzothiophene, pyrrole, pyridine, pyrimidine, pyridazine, pyrazine, quinoline, isoquinoline, phthalazine, benzo-1,2,5-thiadiazole, benzothiazole, triazole, pyrazole, isoxazole, indole, benzotriazole, benzodioxolane, benzodioxane, benzimidazole, carbazole and quinazoline.

The term "condensed" according to the present invention means that a ring or ring-system is attached to another ring or ring-system, whereby the terms "annulated" or "annelated" are also used by those skilled in the art to designate this kind of attachment.

The term "ring system" according to the present invention refers to ring systems comprising saturated, unsaturated or aromatic carbocyclic ring systems which contain optionally at least one heteroatom as ring member and which are optionally at least mono-substituted. Said ring systems may be condensed to other carbocyclic ring systems such as aryl groups, naphtyl groups, heteroaryl groups, cycloalkyl groups, etc.

"Cyclyl groups/radicals" or "cyclic systems", as defined in the present invention, comprise any saturated, unsaturated or aromatic carbocyclic ring systems which contain optionally at least one heteroatom as ring member and which are optionally at least mono-substituted. Cyclyl groups or cyclic systems preferably comprise aryl, heteroaryl, cyclyl, heterocylcyl and/or spiro ring systems.

"Heterocyclyl groups/radicals" or "heterocyclic systems", as defined in the present invention, comprise any saturated, unsaturated or aromatic carbocyclic ring systems which are optionally at least mono-substituted and which contain at least one heteroatom as ring member. Preferred heteroatoms for these heterocyclyl groups are N, S or O. Preferred substituents for heterocyclyl radicals, according to the present invention, are F, Cl, Br, I, NH$_2$, SH, OH, SO$_2$, CF$_3$, carboxy, amido, cyano, carbamyl, nitro, phenyl, benzyl, —SO$_2$NH$_2$, $C_{1-6}$ alkyl and/or $C_{1-6}$-alkoxy.

The term "salt" is to be understood as meaning any form of the active compound according to the invention in which this assumes an ionic form or is charged and is coupled with a counter-ion (a cation or anion) or is in solution. By this are also to be understood complexes of the active compound with other molecules and ions, in particular complexes which are complexed via ionic interactions.

The term "physiologically acceptable salt" or "pharmaceutically acceptable salt" is understood in particular, in the context of this invention, as salt (as defined above) formed either with a physiologically tolerated acid, that is to say salts of the particular active compound with inorganic or organic acids which are physiologically tolerated—especially if used on humans and/or mammals—or with at least one, preferably inorganic, cation which are physiologically tolerated—especially if used on humans and/or mammals. Examples of physiologically tolerated salts of particular acids are salts of: hydrochloric acid, hydrobromic acid, sulfuric acid, hydrobromide, monohydrobromide, monohydrochloride or hydrochloride, methiodide, methanesulfonic acid, formic acid, acetic acid, oxalic acid, succinic acid, malic acid, tartaric acid, mandelic acid, fumaric acid, lactic acid, citric acid, glutamic acid, hippuric acid picric acid and/or aspartic acid. Examples of physiologically tolerated salts of particular bases are salts of alkali metals and alkaline earth metals and with $NH_4$.

The term "solvate" is to be understood as meaning any form of the active compound according to the invention in which this compound has attached to it via non-covalent binding another molecule (most likely a polar solvent) especially including hydrates and alcoholates, e.g. methanolate.

The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the compounds of the invention: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

Any compound that is a prodrug of a compound of formula (I) is within the scope of the invention. Particularly favored prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

In a particular preferred embodiment of the invention $R_1$ $R_2$ and $R_3$ are independently selected from hydrogen or $C_{1-6}$ alkyl.

In another preferred embodiment of the invention $R_4$ and $R_5$ together with the bridging nitrogen form a group selected from:

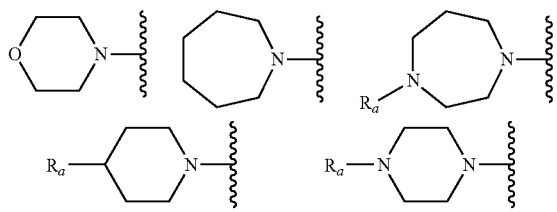

where each $R_a$ is independently selected from H, a $C_{1-6}$ alkyl or a phenyl group optionally substituted by a halogen.

In yet another preferred embodiment of the invention $R_6$ is a group selected from:

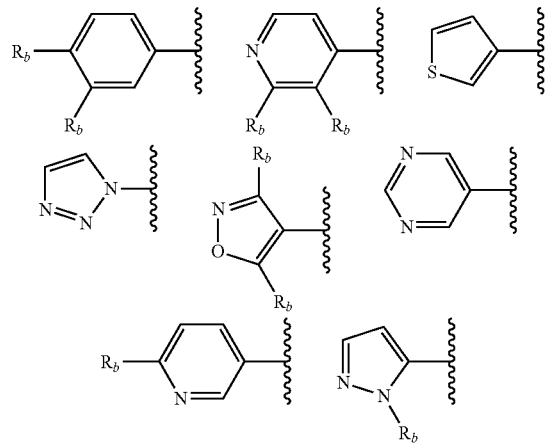

where each $R_b$ is independently selected from H, a $C_{1-6}$ alkyl, a halogen or an —OR' group where R' represents a linear or branched $C_{1-6}$-alkyl group.

The preferred embodiment of the invention comprises compounds of formula (I) where $R_1$ $R_2$ and $R_3$ are independently selected from hydrogen or $C_{1-6}$ alkyl;

$R_4$ and $R_5$ together with the bridging nitrogen form a group selected from:

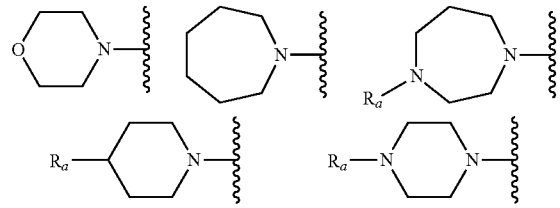

where each $R_a$ is independently selected from H, a $C_{1-6}$ alkyl or a phenyl group optionally substituted by a halogen;

$R_6$ is a group selected from:

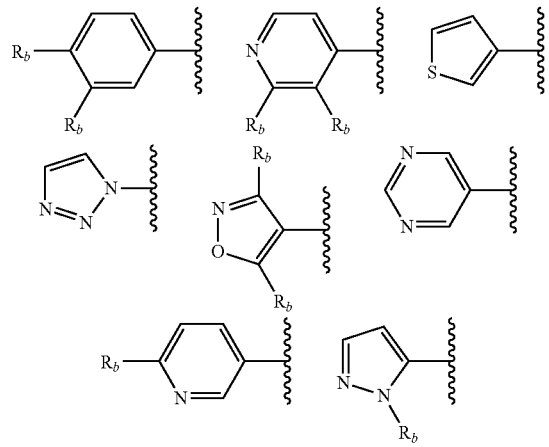

where each $R_b$ is independently selected from H, a $C_{1-6}$ alkyl, a halogen or —OR' group where R' represents a linear or branched $C_{1-6}$-alkyl group.

In preferred variants of the invention, the sigma ligand of formula (I) is selected from:

[1] 4-(2-(7-phenyl-1H-inden-3-yl)ethyl)morpholine maleate,
[2] 1-(2-(7-(4-fluorophenyl)-1H-inden-3-yl)ethyl)azepane hydrochloride,
[3] 4-(2-(7-(pyridin-4-yl)-1H-inden-3-yl)ethyl)morpholine maleate,
[4] 1-(2-(7-(3-fluoropyridin-4-yl)-1H-inden-3-yl)ethyl)-4-methylpiperazine maleate,
[5] 1-methyl-4-(2-(7-phenyl-1H-inden-3-yl)ethyl)piperazine maleate,
[6] 1-phenyl-4-(2-(7-phenyl-1H-inden-3-yl)ethyl)piperazine maleate,
[7] 1-(3-chlorophenyl)-4-(2-(7-phenyl-1H-inden-3-yl)ethyl)piperazine maleate,
[8] 1-(2-(7-phenyl-1H-inden-3-yl)ethyl)piperidine maleate,
[9] 1-(2-(7-phenyl-1H-inden-3-yl)ethyl)azepane maleate,
[10] 4-phenyl-1-(2-(7-phenyl-1H-inden-3-yl)ethyl)piperidine maleate,
[11] 4-(2-(2-methyl-7-phenyl-1H-inden-3-yl)ethyl)morpholine maleate,
[12] 1-methyl-4-(2-(2-methyl-7-phenyl-1H-inden-3-yl)ethyl)piperazine maleate,
[13] 4-(2-(7-(4-fluorophenyl)-1H-inden-3-yl)ethyl)morpholine maleate,
[14] 1-(2-(7-(4-fluorophenyl)-1H-inden-3-yl)ethyl)-4-phenylpiperazine maleate,
[15] 1-(2-(7-(4-fluorophenyl)-1H-inden-3-yl)ethyl)piperidine maleate,
[16] 1-(2-(7-(4-fluorophenyl)-1H-inden-3-yl)ethyl)-4-methylpiperazine maleate,
[17] 1-(2-(7-(3-fluorophenyl)-1H-inden-3-yl)ethyl)-4-methylpiperazine maleate,
[18] 4-(2-(7-(3-fluorophenyl)-1H-inden-3-yl)ethyl)morpholine maleate,
[19] 4-(2-(7-(3,4-dichlorophenyl)-1H-inden-3-yl)ethyl)morpholine maleate,
[20] 1-(2-(7-(3,4-dichlorophenyl)-1H-inden-3-yl)ethyl)-4-methylpiperazine maleate,
[21] 4-(2-(7-(4-methoxyphenyl)-1H-inden-3-yl)ethyl)morpholine maleate,
[22] 1-(2-(7-(4-methoxyphenyl)-1H-inden-3-yl)ethyl)-4-methylpiperazine maleate,
[23] 1-(2-(7-(3,4-dimethoxyphenyl)-1H-inden-3-yl)ethyl)-4-methylpiperazine maleate,
[24] 4-(2-(7-(3,4-dimethoxyphenyl)-1H-inden-3-yl)ethyl)morpholine maleate,
[25] 4-(2-(7-(thiophen-3-yl)-1H-inden-3-yl)ethyl)morpholine maleate,
[26] 1-methyl-4-(2-(7-(thiophen-3-yl)-1H-inden-3-yl)ethyl)piperazine maleate,
[27] 1-(2-(7-(1H-1,2,3-triazol-1-yl)-1H-inden-3-yl)ethyl)-4-methylpiperazine maleate,
[28] 3,5-dimethyl-4-(3-(2-(4-methylpiperazin-1-yl)ethyl)-1H-inden-7-yl)isoxazole maleate,
[29] 5-(3-(2-(4-methylpiperazin-1-yl)ethyl)-1H-inden-7-yl)pyrimidine maleate,
[30] 1-methyl-4-(2-(7-(pyridin-4-yl)-1H-inden-3-yl)ethyl)piperazine maleate,
[31] 1-methyl-4-(2-(7-(pyridin-4-yl)-1H-inden-3-yl)ethyl)-1,4-diazepane maleate,
[32] 1-methyl-4-(2-(2-methyl-7-(pyridin-4-yl)-1H-inden-3-yl)ethyl)piperazine maleate,
[33] 1-(2-(7-(2-fluoropyridin-4-yl)-1H-inden-3-yl)ethyl)-4-methylpiperazine maleate,
[34] 4-(2-(7-(pyridin-3-yl)-1H-inden-3-yl)ethyl)morpholine maleate,
[35] 1-methyl-4-(2-(7-(pyridin-3-yl)-1H-inden-3-yl)ethyl)piperazine maleate,
[36] 1-(2-(7-(6-methoxypyridin-3-yl)-1H-inden-3-yl)ethyl)-4-methylpiperazine maleate,
[37] 1-(2-(7-(6-fluoropyridin-3-yl)-1H-inden-3-yl)ethyl)-4-methylpiperazine maleate,
[38] 1-methyl-4-(2-(7-(1-methyl-1H-pyrazol-5-yl)-1H-inden-3-yl)ethyl)piperazine maleate,
[39] 4-(2-(7-(6-methoxypyridin-3-yl)-1H-inden-3-yl)ethyl)morpholine maleate,
[40] 1-methyl-4-(2-(6-pyridin-4-yl)-1H-inden-3-yl)ethyl)piperazine maleate,
[41] 1-(2-(6-(2-fluoropyridin-4-yl)-1H-inden-3-yl)ethyl)-4-methylpiperazine maleate, or a pharmaceutically acceptable salt, prodrug or solvate thereof.

Any compound referred to herein is intended to represent such specific compound as well as certain variations or forms. In particular, compounds referred to herein may have asymmetric centers and therefore exist in different enantiomeric or diastereomeric forms. Thus, any given compound referred to herein is intended to represent any one of a racemate, one or more enantiomeric forms, one or more diastereomeric forms, and mixtures thereof. Likewise, stereoisomerism or geometric isomerism about the double bond is also possible, therefore in some cases the molecule could exist as (E)-isomer or (Z)-isomer (trans and cis isomers). If the molecule contains several double bonds, each double bond will have its own stereoisomerism, that could be the same as, or different to, the stereoisomerism of the other double bonds of the molecule. Furthermore, compounds referred to herein may exist as atropisomers. All the stereoisomers including enantiomers, diastereoisomers, geometric isomers and atropisomers of the compounds referred to herein, and mixtures thereof, are considered within the scope of the present invention.

Furthermore, any compound referred to herein may exist as tautomers. Specifically, the term tautomer refers to one of two or more structural isomers of a compound that exist in equilibrium and are readily converted from one isomeric form to another. Common tautomeric pairs are amine-imine, amide-imidic acid, keto-enol, lactam-lactim, etc.

Unless otherwise stated, the compounds of the invention are also meant to include isotopically-labelled forms i.e. compounds which differ only in the presence of one or more isotopically-enriched atoms. For example, compounds having the present structures except for the replacement of at least one hydrogen atom by a deuterium or tritium, or the replacement of at least one carbon by $^{13}C$- or $^{14}C$-enriched carbon, or the replacement of at least one nitrogen by $^{15}N$-enriched nitrogen are within the scope of this invention.

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

In another aspect, the invention refers to the processes for obtaining the compounds of general formula (I). Two procedures have been developed for obtaining all the compound derivatives of the invention, herein the procedures will be explained below in methods A and B.

Method A

In a first process, compounds general formula (I):

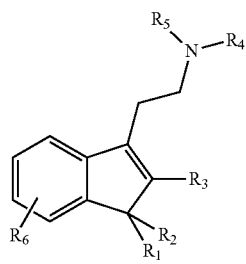

where $R_1$, $R_2$, $R_3$, $R_4$, $R_5$ and $R_6$ have the same meanings as defined above, are prepared by reaction between a compound of general formula (II):

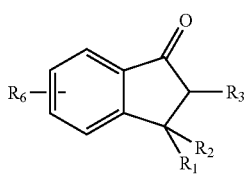

and a compound of general formula (III):

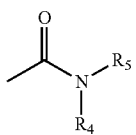

in the presence of a base in an inert solvent, followed by a reduction in the presence of a protic acid and a dehydrating agent.

The general route for the synthesis of compounds of formula (I) by method A is represented in scheme 1:

Scheme 1

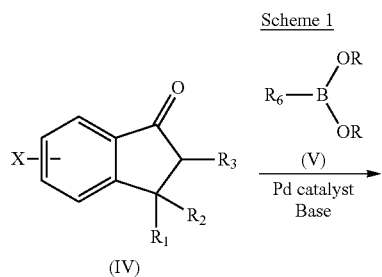

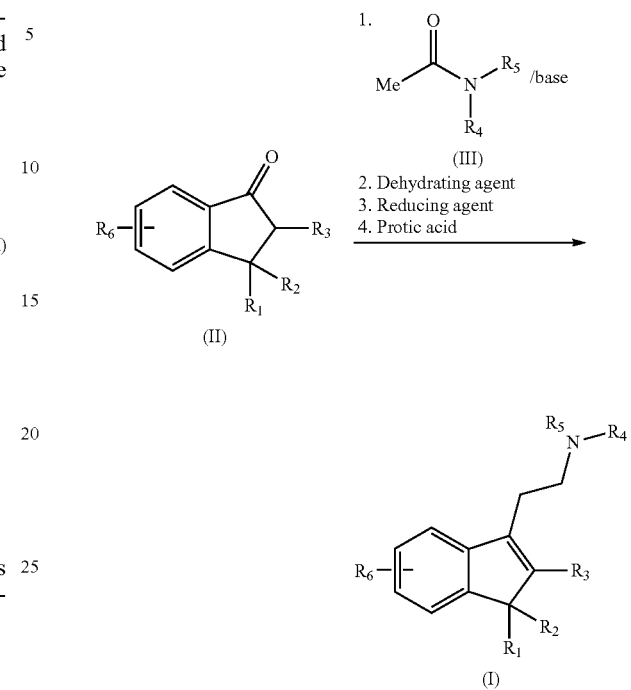

The process for obtaining compounds of formula (I) by method A comprises an Aldol-type condensation of a compound of formula (II) with acetamides (III) in the presence of a base and a suitable solvent; followed by reduction of amide group and isomerization.

This reaction is conducted in a reaction-inert solvent, such as tetrahydrofuran (THF), dimethylsulfoxide (DMSO), 1,2-dimethoxyethane (DME), dimethylformamide (DMF), etc. The base is used must be strong enough to detract a hydrogen from the acetyl group, for example a strong lithiated base, such as lithium diisopropylamide (LDA), lithium hexamethyldisilazide (LHMDS), buthyllithium (BuLi), etc. The dehydrating agent may be selected from an acid, e. g. trifluoroacetic acid (TFA), aqueous $H_2SO_4$, p-toluenesulfonic acid or aqueous solutions of $H_2SO_4$ and acetic acid. The reducing agent may be selected from an inorganic hydride, e. g. lithium aluminum hydride or aluminum hydride, and the protic acid from a solution of an inorganic acid, e. g. sulfuric acid or hydrochloric acid in a suitable solvent.

Compounds of formula (II) are obtained by a Suzuki coupling between halogenated indanones (IV) and organoboronic acid derivatives (V) by methods generally known by the skilled in the art (*J. Med. Chem.* 2005, 48, 5131; *Org. Lett.* 2010, 228).

Acetamides (III) are commercially available or may be obtained by N-acetylation between and a convenient substituted amine and acetic anhydride in a suitable solvent such as ethanol.

Halogenated indanones (IV) and organoboronic acid derivatives (V) are commercially available.

Method B

In a second process compounds of general formula (I):

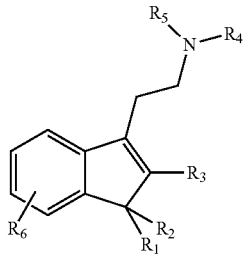
(I)

where $R_1$, $R_2$, $R_3$, $R_4$, $R_5$ and $R_6$ have the same meanings as mentioned above, are prepared by reaction between a compound of general formula (VI):

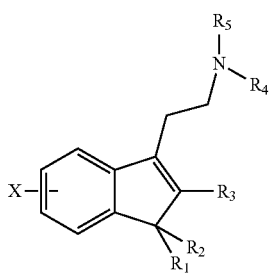
(VI)

where X is a halogen, and a compound of general formula (V):

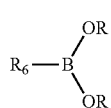
(V)

where each R independently represent a hydrogen, a $C_{1-6}$ alkyl or both R together with the bridging boron form a boronic cyclic ester such as a boronic acid pinacol ester, in the presence of a base, in an inert solvent and optionally in the presence of a catalyst.

The general route for the synthesis of compounds of formula (I) by method B is represented in scheme 2:

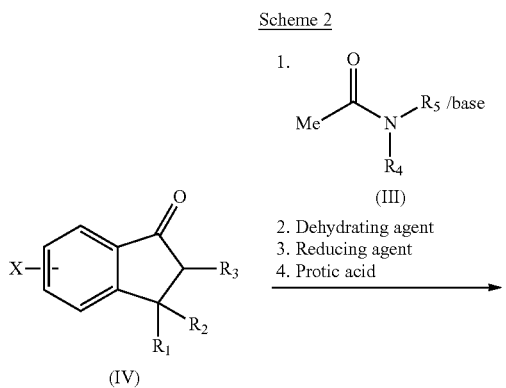

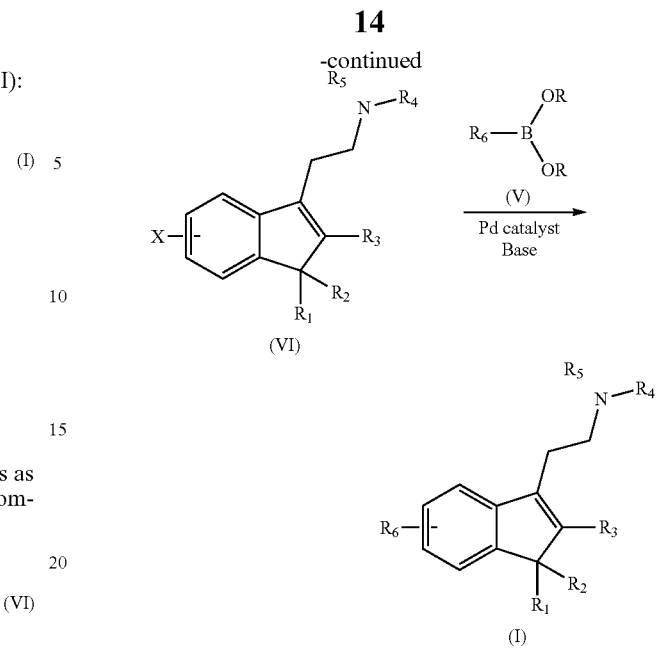

The process for obtaining compounds of formula (I) by method B comprises a Suzuki coupling of a compound of formula (VI) with organoboronic acid derivatives (V) in the presence of a suitable catalyst, for instance a palladium catalyst, a base and a suitable solvent.

This reaction is conducted in a reaction-inert solvent, such as tetrahydrofuran (THF), dimethylsulfoxide (DMSO), dimethylformamide (DMF), diethyl ether, ethanol, water, etc. The palladium catalyst may be selected from a Pd(II) or Pd(0) catalyst, e. g. $Pd(OAc)_2$, $Pd(PPh_3)_4$ or Pd/C. The base that is involved in the coordination sphere of the palladium and in the acceleration of the transmetallation step, may be selected from a negatively charged base, such as sodium or potassium carbonate, phosphate, hydroxide, alkoxides, etc. (*J. Med. Chem.* 2005, 48, 5131; *Org. Lett.* 2010, 228).

Compounds of formula (VI) are obtained by an aldol-type condensation between acetamide (III) and a halogenated indanone (IV) in the presence of a base and a suitable solvent, followed by reduction of amide group and isomerization (see method A).

Acetamides (III) are commercially available or may be obtained by N-acetylation between and a convenient substituted amine and acetic anhydride in a suitable solvent such as ethanol.

Halogenated indanones (IV) and organoboronic acid derivatives (V) are commercially available.

An additional aspect of the invention relates to the therapeutic use of the compounds of general formula (I). As mentioned above, compounds of general formula (I) show a strong affinity to sigma receptors and can behave as agonists, antagonists, inverse agonists, partial antagonists or partial agonists thereof.

Therefore, compounds of general formula (I) are useful as medicaments. They are suitable for the treatment and the prophylaxis of disorders and diseases mediated by sigma receptors, especially, sigma-1 receptors. In this sense, compounds of formula (I) are very good anxiolitic and immunosuppressant and are very useful in the treatment and prophylaxis of diarrhoea, lipoprotein disorders, hyperlipidemia, hypertriglyceridemia, hypercholesterolemia, obesity, migraine, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer, psychotic conditions, in particular depression, anxiety or schizophrenia; inflammation or autoimmune diseases.

The compounds of formula (I) are especially suited for the treatment of pain, especially neuropathic pain, inflammatory pain or other pain conditions involving allodynia and/or hyperalgesia. PAIN is defined by the International Association for the Study of Pain (IASP) as "an unpleasant sensory and emotional experience associated with actual or potential tissue damage, or described in terms of such damage (IASP, Classification of chronic pain, 2nd Edition, IASP Press (2002), 210). Even though pain is always subjective its causes or syndromes can be classified.

In a preferred embodiment compounds of the invention are used for the treatment and prophylaxis of allodynia and more specifically mechanical or thermal allodynia.

In another preferred embodiment compounds of the invention are used for the treatment and prophylaxis of hyperalgesia.

In yet another preferred embodiment compounds of the invention are used for the treatment and prophylaxis of neuropathic pain and more specifically for the treatment and prophylaxis of hyperpathia.

A related aspect of the invention refers to the use of compounds of formula (I) for the manufacture of a medicament for the treatment of disorders and diseases mediated by sigma receptors, as explained before.

Another aspect of the invention is a pharmaceutical composition which comprises at least a compound of general formula (I) or a pharmaceutically acceptable salt, prodrug, isomer or solvate thereof, and at least a pharmaceutically acceptable carrier, additive, adjuvant or vehicle.

The pharmaceutical composition of the invention can be formulated as a medicament in different pharmaceutical forms comprising at least a compound binding to the sigma receptor and optionally at least one further active substance and/or optionally at least one auxiliary substance.

The auxiliary substances or additives can be selected among carriers, excipients, support materials, lubricants, fillers, solvents, diluents, colorants, flavour conditioners such as sugars, antioxidants and/or agglutinants. In the case of suppositories, this may imply waxes or fatty acid esters or preservatives, emulsifiers and/or carriers for parenteral application. The selection of these auxiliary materials and/or additives and the amounts to be used will depend on the form of application of the pharmaceutical composition.

The pharmaceutical composition in accordance with the invention can be adapted to any form of administration, be it orally or parenterally, for example pulmonarily, nasally, rectally and/or intravenously.

Preferably, the composition is suitable for oral or parenteral administration, more preferably for oral, intravenous, intraperitoneal, intramuscular, subcutaneous, intrathekal, rectal, transdermal, transmucosal or nasal administration.

The composition of the invention can be formulated for oral administration in any form preferably selected from the group consisting of tablets, drageés, capsules, pills, chewing gums, powders, drops, gels, juices, syrups, solutions and suspensions.

The composition of the present invention for oral administration may also be in the form of multiparticulates, preferably microparticles, microtablets, pellets or granules, optionally compressed into a tablet, filled into a capsule or suspended in a suitable liquid. Suitable liquids are known to those skilled in the art.

Suitable preparations for parenteral applications are solutions, suspensions, reconstitutable dry preparations or sprays.

The compounds of the invention can be formulated as deposits in dissolved form or in patches, for percutaneous application.

Skin applications include ointments, gels, creams, lotions, suspensions or emulsions.

The preferred form of rectal application is by means of suppositories.

The respective medicament may—depending on its route of administration—also contain one or more auxiliary substances known to those skilled in the art. The medicament according to the present invention may be produced according to standard procedures known to those skilled in the art.

The daily dosage for humans and animals may vary depending on factors that have their basis in the respective species or other factors, such as age, sex, weight or degree of illness and so forth. The daily dosage for humans may preferably be in the range from 1 to 2000, preferably 1 to 1500, more preferably 1 to 1000 milligrams of active substance to be administered during one or several intakes per day.

The following examples are merely illustrative of certain embodiments of the invention and cannot be considered as restricting it in any way.

EXAMPLES

Example 1 (Method A)

Synthesis of 4-(2-(7-phenyl-1H-inden-3-yl)ethyl morpholine maleate a) Synthesis of 4-phenyl-2,3-dihydro-1H-inden-1-one

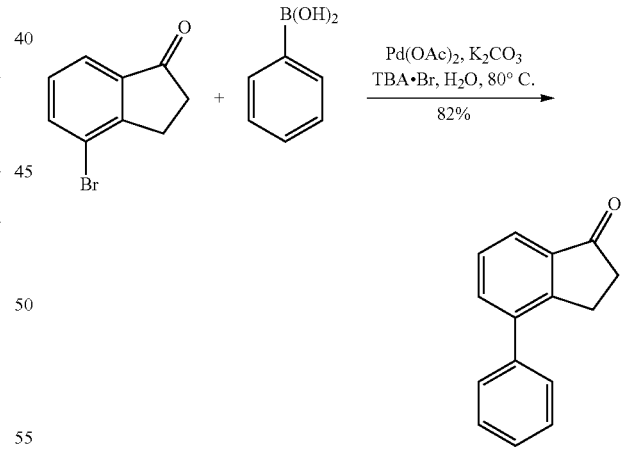

A mixture of 4-bromoindan-1-one (500 mg, 2.36 mmol), phenylboronic acid (317 mg, 2.6 mmol), tetrabutylammonium bromide (761 mg, 2.36 mmol), and $K_2CO_3$ (3.26 g, 23.6 mmol) was suspended in argon-purged water (7.0 mL) and purged with argon for an additional 15 minutes. $Pd(OAc)_2$ (6.0 mg, 0.024 mmol) was added, and the resulting suspension was heated for 3 h at 80° C. After the solution had cooled to room temperature it was diluted with water and extracted with $CH_2Cl_2$. The combined extracts were dried over $Na_2SO_4$, and evaporated to dryness. The residue obtained was purified by silica gel column chromatography (hexane: CH$_2$Cl$_2$ mixtures of increasing polarity as eluent) to yield the desired product as a yellow solid (404 mg, 82%).

$^1$H-NMR (CDCl$_3$, 400 MHz) δ: 7.78 (dd, J=7.6, 1.2 Hz, 1H), 7.6 (dd, J=7.2, 1.2 Hz, 1H), 7.50-7.45 (m, 5H), 7.41 (m, 1H), 3.17 (t, J=6 Hz, 2H), 2.70 (m, 2H) ppm.

EI-MS m/z: 208.1 (M).

b) Synthesis of 4-(2-(7-phenyl-1H-inden-3-yl)ethyl)morpholine maleate

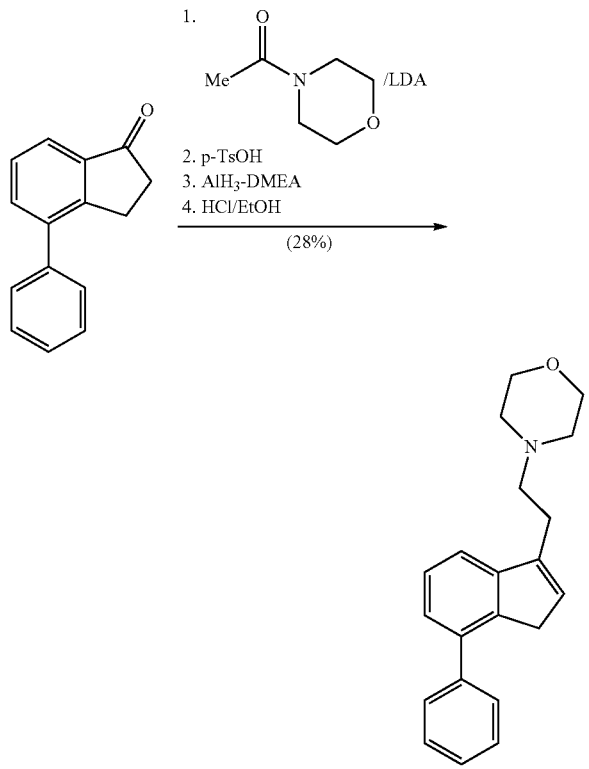

To 4 mL of THF cooled to −78° C., a solution of LDA (1.5 M in THF, 2 mL, 2.95 mmol) was added, under argon atmosphere. Then, N-acetylmorpholine (274 μL, 2.36 mmol) was added and the resulting mixture was stirred at −78° C. for 1 h. Finally, a solution of 4-phenyl-2,3-dihydro-1H-inden-1-one (246 mg, 1.18 mmol) in THF (10 mL) was added, and the resulting mixture was kept at −78° C. for 4 h. The reaction mixture was acidified with 1N HCl and extracted with EtOAc. The organic extracts were dried over Na$_2$SO$_4$ and evaporated to dryness. To a solution of the previous residue in CH$_2$Cl$_2$ (12 mL) p-toluenesulfonic acid (30 mg, 0.12 mmol) was added and the resulting mixture was stirred overnight. The reaction mixture was basified with saturated NaHCO$_3$ aqueous solution and extracted with CH$_2$Cl$_2$. The organic extract was dried over Na$_2$SO$_4$ and evaporated to dryness. To a solution of the previous residue in THF (15 mL) cooled to 0° C., AlH$_3$—NMe$_2$Et (0.5 M in toluene, 4.8 mL, 2.38 mmol) was added and the resulting mixture was stirred for 5 h. EtOAc:H$_2$O (40 mL, 1:1) was added to the reaction mixture and the resulting suspension was filtered through Celite®. The layers were separated and the aqueous phase was extracted with EtOAc. The organic extract, after being dried over Na$_2$SO$_4$, was evaporated to dryness. A solution of the previous residue in 37% HCl:EtOH (30 mL, 1:1) was refluxed overnight. The reaction mixture was evaporated to dryness, dissolved in water, basified with KOH, and extracted with EtOAc. The organic layers were dried with Na$_2$SO$_4$ and evaporated to dryness. Purification of the residue by silica gel column chromatography (hexane:EtOAc mixtures of increasing polarity as eluent) afforded the desired product (100 mg, 28%). The product was converted into the corresponding maleate salt by adding maleic acid (39 mg, 0.33 mmol) in acetone (0.6 mL), followed by filtration of the resulting solid and drying under vacuum.

$^1$H-NMR (DMSO-d$_6$, 300 MHz) δ: 7.60 (dd, J=8.4, 1.5 Hz, 2H), 7.50-7.44 (m, 4H), 7.40 (m, 1H), 7.26 (dd, J=6.0, 2.4 Hz, 1H), 6.40 (s, 1H), 6.04 (s, 2H), 3.79 (m, 4H), 3.47 (s, 2H), 3.31 (m, 8H), 2.95 (m, 2H) ppm.

ESI(+)-HRMS: 306.1852 [M+H]$^+$.

Example 2 (Method A)

Synthesis of 1-(2-(7-(4-fluorophenyl)-1H-inden-3-yl)ethyl)azepane hydrochloride a) Synthesis of 1-(azepan-1-yl)ethanone

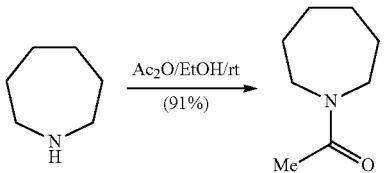 [SMILES: C1CCCNCC1 ; CC(=O)N1CCCCCC1]

To a solution of azepine (2.0 g, 20.17 mmol) in EtOH (30 mL), acetic anhydride (3.8 mL, 40.34 mmol) was added. The resulting solution was stirred overnight. The reaction mixture was evaporated to dryness. Purification of the residue by silica gel column chromatography (CH$_2$Cl$_2$:MeOH mixtures of increasing polarity as eluent) afforded the desired product (2.59 g, 91%).

$^1$H-NMR (CDCl$_3$, 300 MHz) δ: 3.52 (t, J=5.7 Hz, 2H), 3.42 (t, J=6 Hz, 2H), 2.09 (s, 3H), 1.71 (m, 4H), 1.57 (m, 4H) ppm.

b) Synthesis of 4-(4-fluorophenyl)-2,3-dihydro-1H-inden-1-one

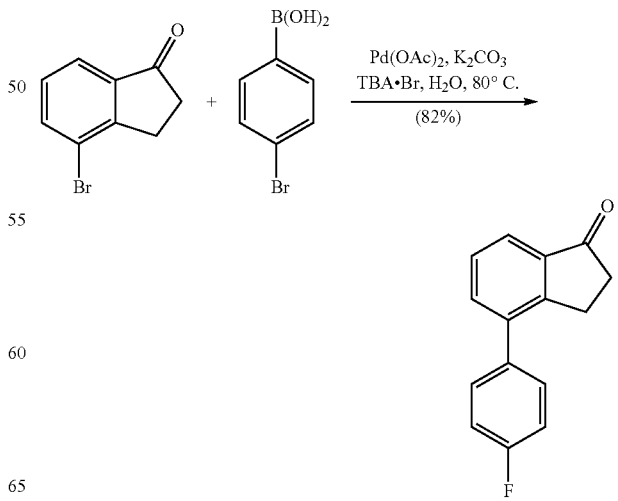

A mixture of 4-bromoindan-1-one (500 mg, 2.36 mmol), (4-fluorophenyl)boronic acid (363 mg, 2.6 mmol), tetrabutylammonium bromide (761 mg, 2.36 mmol), and $K_2CO_3$ (3.26 g, 23.6 mmol) was suspended in argon-purged water (7.0 mL) and purged with argon for an additional 15 minutes. $Pd(OAc)_2$ (6.0 mg, 0.024 mmol) was added, and the resulting suspension was heated for 4 h at 80° C. After the solution had cooled to room temperature it was diluted with water and extracted with $CH_2Cl_2$. The combined organic extracts were dried over $Na_2SO_4$, and evaporated to dryness. The residue obtained was purified by silica gel column chromatography (hexane:EtOAc mixtures of increasing polarity as eluent) to yield the desired product as a yellow solid (443 mg, 82%).

$^1$H-NMR (CDCl$_3$, 400 MHz) δ: 7.78 (dd, J=7.6, 1.2 Hz, 1H), 7.56 (dd, J=7.2, 1.2 Hz, 1H), 7.47 (d, J=7.6 Hz, 1H), 7.42 (m, 3H), 7.17 (m, 2H), 3.14 (t, J=5.8 Hz, 2H), 2.70 (m, 2H).

EI-MS m/z: 226.1 (M).

c) Synthesis of 1-(2-(7-(4-fluorophenyl)-1H-inden-3-yl)ethyl)azepane

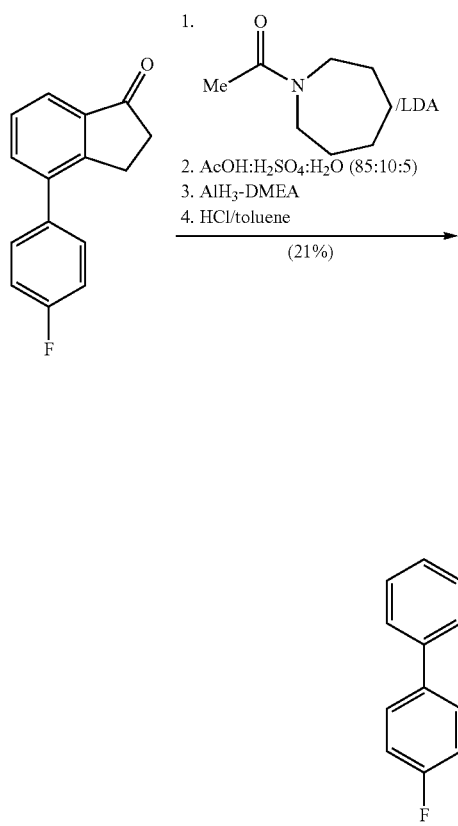

To a solution 1-(azepan-1-yl)ethanone (500 mg, 3.54 mmol) in THF (6 mL) cooled to −78° C., a solution of LDA (1.5 M in THF, 2.9 mL, 4.43 mmol) was added, and the resulting mixture was stirred at −78° C. for 1 h under argon atmosphere. Finally, a solution of 4-(4-fluorophenyl)-2,3-dihydro-1H-inden-1-one (400 mg, 1.77 mmol) in THF (12 mL) was added, and the resulting mixture was kept at −78° C. for 5 h. The reaction mixture was acidified with 1N HCl and extracted with EtOAc. The organic extracts were dried over $Na_2SO_4$ and evaporated to dryness. A solution of the previous residue in AcOH:$H_2SO_4$:$H_2O$ (26 mL, 85:10:5) was stirred for 5 h. The reaction mixture was poured into water, basified with 5 M NaOH and extracted with EtOAc. The organic extract, after being dried over $Na_2SO_4$, was evaporated to dryness. To a solution of the previous residue in THF (20 mL) cooled to 0° C., AlH$_3$—NMe$_2$Et (0.5 M in toluene, 7.9 mL, 3.97 mmol) was added and the resulting mixture was stirred for 4 h. EtOAc:$H_2O$ (20 mL, 1:1) was added to the reaction mixture and the resulting suspension was filtered through Celite®. The layers were separated and the aqueous phase was extracted with EtOAc. The organic extract was dried over $Na_2SO_4$ and evaporated to dryness. A solution of the previous residue in 37% HCl:toluene (44 mL, 1:1) was refluxed overnight. The reaction mixture was evaporated to dryness. Purification of the residue by silica gel column chromatography (EtOAc/NH$_3$:MeOH mixtures of increasing polarity as eluent) afforded the desired product (116 mg, 21%). The product were converted into the corresponding hydrochloride salt by adding a solution of HCl (1M in diethyl ether, 0.25 mL) followed by filtration of the resulting solid and drying under vacuum.

$^1$H-NMR (DMSO-d$_6$, 400 MHz) δ: 9.90 (s, 1H), 7.64 (m, 2H), 7.51 (d, J=6.4 Hz, 1H), 7.44 (t, J=7.6 Hz, 1H), 7.31-7.25 (m, 2H), 6.45 (s, 1H), 3.48 (m, 2H), 3.41 (m, 2H), 3.31 (s, 4H), 3.20 (m, 2H), 3.01 (m, 2H), 1.84 (4H), 1.64 (m, 4H) ppm.

ESI(+)-HRMS: 336.2021 [M+H]$^+$

Example 3 (Method A)

Synthesis of 4-(2-(7-(pyridin-4-yl)-1H-inden-3-yl)ethyl)morpholine maleate a) Synthesis of 4(-pyridin-4-yl)-2,3-dihydro-1H-inden-1-one

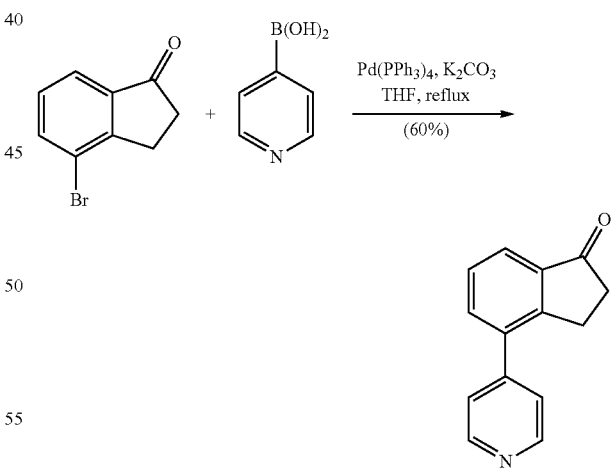

A mixture of 4-bromoindan-1-one (1.25 g, 5.90 mmol), Pd(PPh$_3$)$_4$ (1.7 g, 1.48 mmol), pyridin-4-ylboronic acid (940 mg, 6.49 mmol) and 2 M solution of K$_2$CO$_3$ (15 mL) in THF (70 mL) was refluxed with stirring for 1 day under argon atmosphere. The reaction mixture was extracted with 1N HCl. The aqueous layers were basified with 2N NaOH and extracted with EtOAc. The organic layers were dried with Na$_2$SO$_4$ and evaporated to dryness. Purification of the residue by silica gel column chromatography (hexane:EtOAc mixtures of increasing polarity as eluent) afforded the desired product (756 mg, 60%).

$^1$H-NMR (DMSO-d$_6$, 400 MHz) δ: 8.75 (m, 2H), 7.84 (d, J=7.6 Hz, 1H), 7.63 (dd, J=7.6, 0.8 Hz, 1H), 7.53 (d, J=7.6 Hz, 1H), 7.42 (d, J=5.2 Hz, 2H), 3.19 (t, J=6 Hz, 2H), 2.73 (t, J=5.8 Hz, 2H) ppm.

EI-MS m/z: 209.2 (M).

b) Synthesis of 4-(2-(7-(pyridin-4-yl)-1H-inden-3-yl)ethyl)morpholine

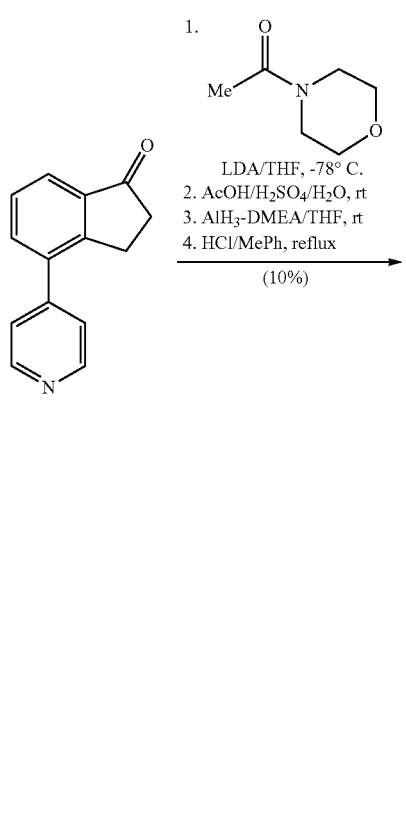

To a solution of N-acetylmorpholine (0.42 mL, 3.61 mmol) in THF (10 mL) cooled to −78° C., a solution of LDA (1.5 M in THF, 3 mL, 4.52 mmol) was added, and the resulting mixture was stirred at −78° C. for 1 h under argon atmosphere. Finally, a solution of 4(-pyridin-4-yl)-2,3-dihydro-1H-inden-1-one (378 mg, 1.81 mmol) in THF (15 mL) was added, and the resulting mixture was kept at −78° C. for 4 h. The reaction mixture was diluted with water and extracted with EtOAc. The organic extracts were dried over Na$_2$SO$_4$ and evaporated to dryness. A solution of the previous residue in AcOH:H$_2$SO$_4$:H$_2$O (28 mL, 85:10:5) was stirred 2.5 days. The reaction mixture was poured into water, basified with 4M NaOH and extracted with EtOAc. The organic extract, after being dried over Na$_2$SO$_4$, was evaporated to dryness. To a solution of the previous residue in THF (12 mL) cooled to 0° C., AlH$_3$—NMe$_2$Et (0.5 M in toluene, 7 mL, 3.49 mmol) was added and the resulting mixture was stirred 4 h. EtOAc:H$_2$O (40 mL, 1:1) was added to the reaction mixture and the resulting suspension was filtered through Celite®. The layers were separated and the aqueous phase was extracted with EtOAc. The organic extract, after being dried over Na$_2$SO$_4$, was evaporated to dryness. A solution of the previous residue in 37% HCl:toluene (50 mL, 1:1) was refluxed overnight. Purification of the residue by silica gel column chromatography (EtOAc/NH$_3$:MeOH mixtures of increasing polarity as eluent) afforded the desired product (54 mg, 10%). The product were converted into the corresponding maleate salt by adding maleic acid (20 mg, 0.18 mmol) in acetone (0.3 mL), followed by filtration of the resulting solid and drying under vacuum.

$^1$H-NMR (DMSO-d$_6$, 400 MHz) δ: 8.65 (d, J=5.2 Hz, 2H), 7.65 (d, J=4.4 Hz, 2H), 7.56-7.48 (m, 2H), 7.37 (dd, J=7.4, 1 Hz, 1H), 6.48 (s, 1H), 6.05 (s, 2H), 3.82 (m, 4H), 3.55 (s, 2H), 3.36 (m, 2H), 3.25 (m, 4H), 2.96 (m, 2H) ppm.

ESI(+)-HRMS: 307.1809 [M+H]$^+$

Example 4 (Method B)

Synthesis of 1-(2-(7-(3-fluoropyridin-4-yl)-1H-inden-3-yl)ethyl)-4-methylpiperazine maleate a) Synthesis of 1-(4-methylpiperazin-1-yl)ethanone

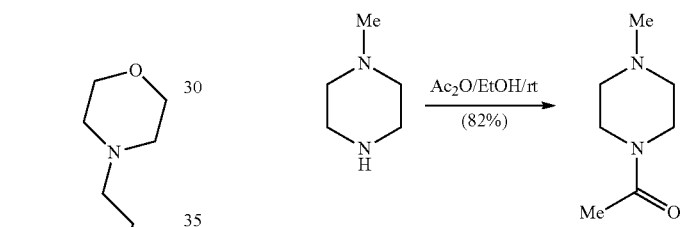

A solution of N-methylpiperazine (2.0 g, 19.97 mmol), triethylamine (3.35 mL, 23.96 mmol) and acetic anhydride (2.3 mL, 23.96 mmol) in EtOH (60 mL) was stirred at room temperature overnight. The reaction mixture was evaporated to dryness. Purification of the residue by silica gel column chromatography (CH$_2$Cl$_2$:MeOH mixtures of increasing polarity as eluent) afforded the desired product (2.16 g, 76%) as a yellow oil.

$^1$H-NMR (CDCl$_3$, 300 MHz) δ: 3.65 (t, J=6.8 Hz, 2H), 3.49 (t, J=6.8 Hz, 2H), 2.46-2.39 (m, 4H), 2.32 (s, 3H), 2.10 (s, 3H) ppm.

b) Synthesis of 1-(2-(7-bromo-1H-inden-3-yl)ethyl)-4-methylpiperazine

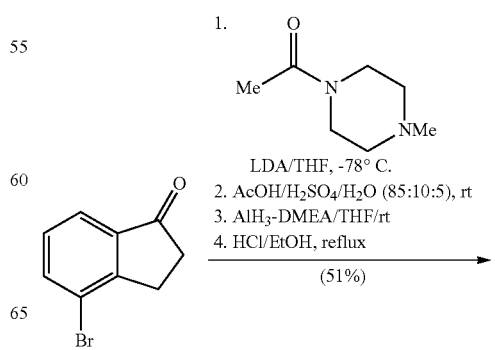

c) Synthesis of 1-(2-(7-(3-fluoropyridin-4-yl)-1H-inden-3-yl)ethyl)-4-methylpiperazine maleate

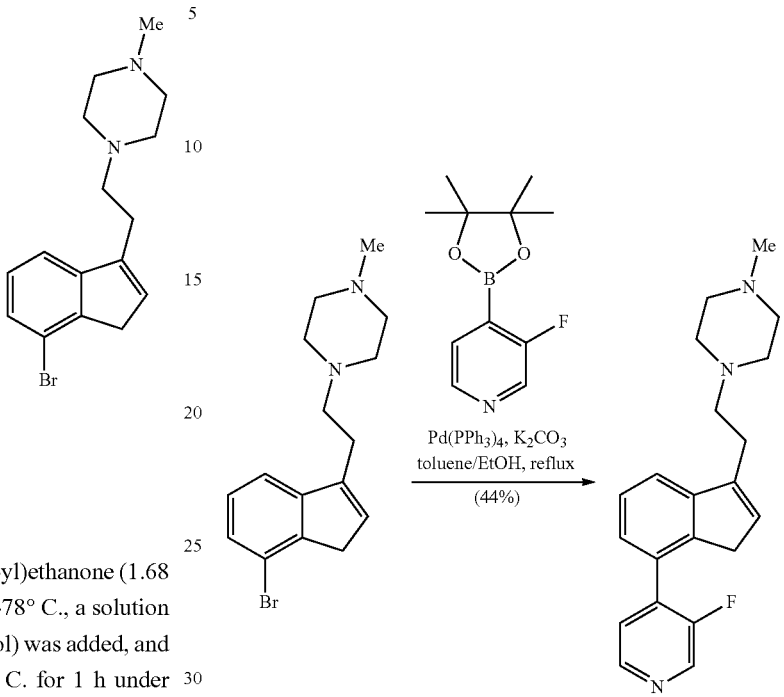

To a solution of 1-(4-methylpiperazin-1-yl)ethanone (1.68 g, 11.8 mmol) in THF (25 mL) cooled to −78° C., a solution of LDA (1.5 M in THF, 9.8 mL, 14.75 mmol) was added, and the resulting mixture was stirred at −78° C. for 1 h under argon atmosphere. Finally, a solution of 4-bromoindan-1-one (1.25 g, 5.9 mmol) in THF (50 mL) was added, and the resulting mixture was kept at −78° C. for 4 h. The reaction mixture was diluted with water and extracted with EtOAc. The organic extracts were dried over $Na_2SO_4$ and evaporated to dryness. A solution of the previous residue in $AcOH:H_2SO_4:H_2O$ (79 mL, 85:10:5) was stirred for 6 h. The reaction mixture was poured into water, basified with 50% NaOH and extracted with EtOAc. The organic extract, after being dried over $Na_2SO_4$, was evaporated to dryness. To a solution of the previous residue in THF (75 mL) cooled to 0° C., $AlH_3$—$NMe_2Et$ (0.5 M in toluene, 20 mL, 10.34 mmol) was added and the resulting mixture was stirred for 5 h. $EtOAc:H_2O$ (90 mL, 1:1) was added to the reaction mixture and the resulting suspension was filtered through Celite®. The layers were separated and the aqueous phase was extracted with EtOAc. The organic extract was dried over $Na_2SO_4$ and evaporated to dryness. A solution of the previous residue in 37% HCl:EtOH (150 mL, 1:1) was refluxed overnight. The reaction mixture was evaporated to dryness. Purification of the residue by silica gel column chromatography ($EtOAc/NH_3$:MeOH mixtures of increasing polarity as eluent) afforded the desired product (981 mg, 51%).

$^1$H-NMR (CDCl$_3$, 300 MHz) δ: 7.32 (m, 2H), 7.18 (t, J=7.6 Hz, 1H), 6.30 (s, 1H), 3.31 (d, J=1.8 Hz, 2H), 2.72 (m, 4H), 2.60 (m, 4H), 2.51 (m, 4H), 2.30 (s, 3H) ppm.

EI-MS m/z: 320.1 (M).

A mixture of 1-(2-(7-bromo-1H-inden-3-yl)ethyl)-4-methylpiperazine (150 mg, 0.47 mmol), Pd(PPh$_3$)$_4$ (92 mg, 0.08 mmol), 2-fluoro-4-pyridineboronic acid pinacol ester (364 mg, 1.63 mmol) and 2 M solution of $K_2CO_3$ (4 mL) in toluene:EtOH (17 mL, 4:1) was refluxed with stirring for 1 day under argon atmosphere. The reaction mixture was poured into water and extracted with EtOAc. The aqueous layers were basified with 2N NaOH and extracted with EtOAc. The organic layers were washed with brine, dried with $Na_2SO_4$ and evaporated to dryness. Purification of the residue by silica gel column chromatography ($EtOAc/NH_3$:MeOH mixtures of increasing polarity as eluent) afforded the desired product (70 mg, 44%). The product was converted into the corresponding maleate salt by adding maleic acid (24 mg, 0.21 mmol) in acetone (0.2 mL), followed by filtration of the resulting solid and drying under vacuum.

$^1$H-NMR (DMSO-d$_6$, 400 MHz) δ: 8.32 (d, J=5.2 Hz, 1H), 7.62 (dt, J=5.2, 2 Hz, 1H), 7.53 (dd, J=7.8, 1 Hz, 1H), 7.50-7.45 (m, 2H), 7.39 (d, J=7.4 Hz, 1H), 6.43 (s, 1H), 6.12 (s, 2H), 3.54 (s, 2H), 3.29 (m, 8H), 2.85 (m, 2H), 2.79 (m, 2H), 2.70 (m, 3H) ppm.

ESI(+)-HRMS: 338.2025 [M+H]

The following examples were obtained using the methods (A or B) previously described, as indicated.

| Example | Structure | Method | Name | NMR |
|---|---|---|---|---|
| 5 | 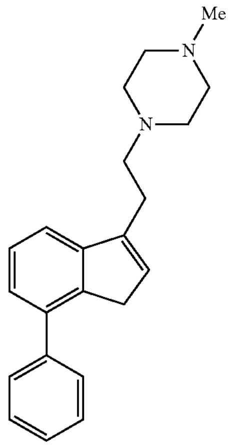 [SMILES: CN1CCN(CCC2=CCc3c2cccc3-c2ccccc2)CC1] | A | 1-Methyl-4-(2-(7-phenyl-1H-inden-3-yl)ethyl)piperazine maleate | $^1$H-NMR (DMSO-$d_6$, 300 MHz) δ: 7.60 (m, 2H), 7.50-7.40 (m, 4H), 7.39 (m, 1H), 7.24 (m, 1H), 6.38 (s, 1H), 6.11 (s, 2H), 3.43 (s, 2H), 3.30 (m, 8H), 2.86 (m, 2H), 2.80 (m, 2H), 2.68 (s, 3H) ppm. |
| 6 | 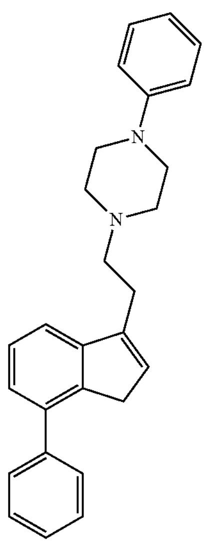 [SMILES: C1=C(CCN2CCN(c3ccccc3)CC2)c2cccc(-c3ccccc3)c2C1] | A | 1-Phenyl-4-(2-(7-phenyl-1H-inden-3-yl)ethyl)piperazine maleate | $^1$H-NMR (DMSO-$d_6$, 400 MHz) δ: 7.60 (m, 2H), 7.50-7.45 (m, 4H), 7.38 (m, 1H), 7.28 (t, J = 7.6 Hz, 3H), 7.02 (d, J = 8 Hz, 2H), 6.86 (t, J = 7.4 Hz, 1H), 6.45 (s, 1H), 6.03 (s, 2H), 3.48 (m, 2H), 3.30 (m, 8H), 3.00 (s, 4H) ppm. |
| 7 | 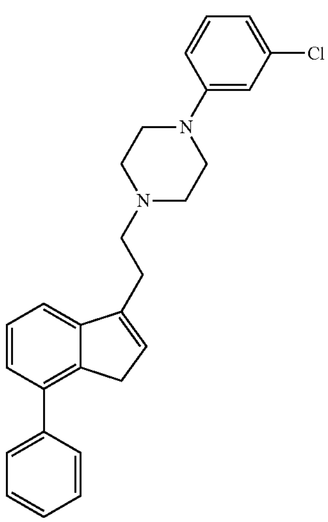 [SMILES: Clc1cccc(N2CCN(CCC3=CCc4c3cccc4-c3ccccc3)CC2)c1] | A | 1-(3-Chlorophenyl)-4-(2-(7-phenyl-1H-inden-3-yl)ethyl)piperazine maleate | $^1$H-NMR (DMSO-$d_6$, 400 MHz) δ: 7.60 (m, 2H), 7.50-7.45 (m, 4H), 7.40 (m, 1H), 7.27 (d, J = 8.4 Hz, 1H), 7.08 (t, J = 2 Hz, 1H), 6.99 (dd, J = 8.4, 2 Hz, 1H), 6.87 (dd, J = 8, 1.1 Hz, 1H), 6.45 (s, 1H), 6.07 (s, 2H), 3.48 (m, 2H), 3.31 (m, 10H), 3.02 (m, 2H) ppm. |

| Example | Structure | Method | Name | NMR |
|---|---|---|---|---|
| 8 | 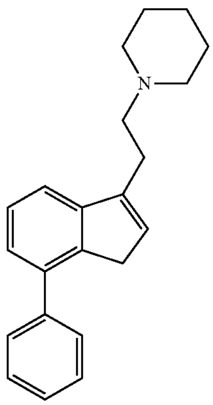 [SMILES: C1=C(CCN2CCCCC2)c2cccc(-c3ccccc3)c2C1] | A | 1-(2-(7-Phenyl-1H-inden-3-yl)ethyl)piperidine maleate | $^1$H-NMR (DMSO-d$_6$, 400 MHz) δ: 9.14 (s, 1H), 7.60 (m, 2H), 7.47-7.45 (m, 4H), 7.39 (m, 1H), 7.27 (dd, J = 7, 1.8 Hz, 1H), 6.44 (s, 1H), 6.01 (s, 2H), 3.57 (m, 2H), 3.47 (m, 2H), 3.38 (m, 2H), 2.98 (m, 4H), 1.87 (m, 2H), 1.68 (m, 3H), 1.39 (m, 1H) ppm. |
| 9 | 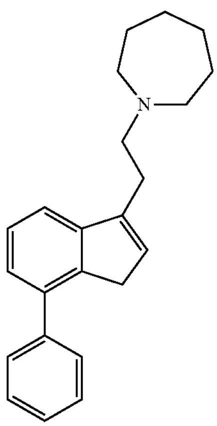 [SMILES: C1=C(CCN2CCCCCC2)c2cccc(-c3ccccc3)c2C1] | A | 1-(2-(7-Phenyl-1H-inden-3-yl)ethyl)azepane maleate | $^1$H-NMR (DMSO-d$_6$, 400 MHz) δ: 9.30 (s, 1H), 7.60 (m, 2H), 7.47-7.44 (m, 4H), 7.41 (m, 1H), 7.27 (dd, J = 7.4, 1.4 Hz, 1H), 6.45 (s, 1H), 6.00 (s, 2H), 3.47-3.42 (m, 6H), 3.24 (m, 2H), 2.97 (m, 2H), 1.86 (m, 4H), 1.64 (m, 4H) ppm. |
| 10 | 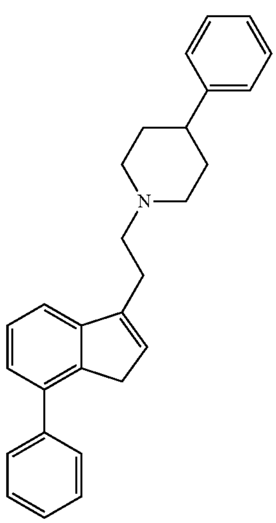 [SMILES: C1=C(CCN2CCC(c3ccccc3)CC2)c2cccc(-c3ccccc3)c2C1] | A | 4-Phenyl-1-(2-(7-phenyl-1H-inden-3-yl)ethyl)piperidine maleate | $^1$H-NMR (DMSO-d$_6$, 400 MHz) δ: 7.60 (m, 2H), 7.50-7.46 (m, 4H), 7.39 (dt, J = 7.6, 1.2 Hz, 1H), 7.35 (t, J = 7.4 Hz, 2H), 7.25-7.29 (m, 4H), 6.47 (s, 1H), 6.01 (s, 2H), 3.75 (m, 2H), 3.49 (m, 4H), 3.16 (m, 2H), 3.03 (m, 2H), 2.85 (m, 1H), 2.05 (m, 2H), 1.89 (m, 2H) ppm. |

-continued

| Example | Structure | Method | Name | NMR |
|---|---|---|---|---|
| 11 | 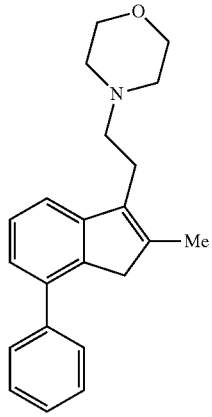 [SMILES: CC1=C(CCN2CCOCC2)c2cccc(-c3ccccc3)c2C1] | A | 4-(2-(2-Methyl-7-phenyl-1H-inden-3-yl)ethyl)morpholine maleate | $^1$H-NMR (DMSO-$d_6$, 400 MHz) δ: 7.56 (m, 2H), 7.46 (td, J = 6.6, 1.6 Hz, 2H), 7.40-7.35 (m, 3H), 7.16 (dd, J = 7, 1.2 Hz, 1H), 6.04 (s, 2H), 3.75 (m, 4H), 3.43 (s, 2H), 3.30 (m, 4H), 3.12 (m, 4H), 2.88 (m, 2H), 2.07 (s, 3H) ppm. |
| 12 | 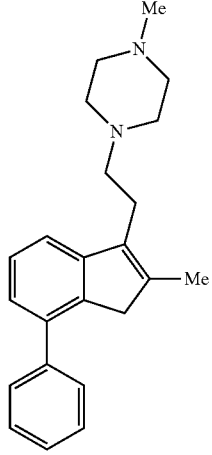 [SMILES: CC1=C(CCN2CCN(C)CC2)c2cccc(-c3ccccc3)c2C1] | A | 1-Methyl-4-(2-(2-methyl-7-phenyl-1H-inden-3-yl)ethyl)piperazine maleate | $^1$H-NMR (DMSO-$d_6$, 400 MHz) δ: 7.56 (dd, J = 8, 1.2 Hz, 2H), 7.46 (t, J = 7.6 Hz, 2H), 7.36 (m, 2H), 7.27 (d, J = 7.6 Hz, 1H), 7.14 (d, J = 7.6 Hz, 1H), 6.09 (s, 2H), 3.39 (s, 2H), 3.08 (m, 9H), 2.72 (m, 2H), 2.68 (m, 4H), 2.06 (s, 3H) ppm. |
| 13 | 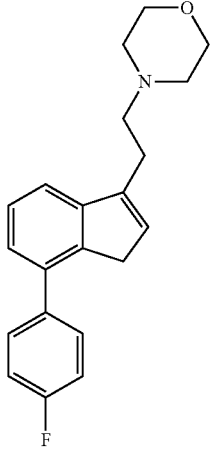 [SMILES: Fc1ccc(-c2cccc3c2CC=C3CCN2CCOCC2)cc1] | A | 4-(2-(7-(4-Fluorophenyl)-1H-inden-3-yl)ethyl)morpholine maleate | $^1$H-NMR (DMSO-$d_6$, 400 MHz) δ: 7.64 (m, 2H), 7.46 (m, 2H), 7.30-7.25 (m, 3H), 6.44 (s, 1H), 6.04 (s, 2H), 3.75 (m, 2H), 3.45 (m, 2H), 3.31 (m, 8H), 2.94 (m, 2H) ppm. |

-continued

| Example | Structure | Method | Name | NMR |
|---|---|---|---|---|
| 14 | 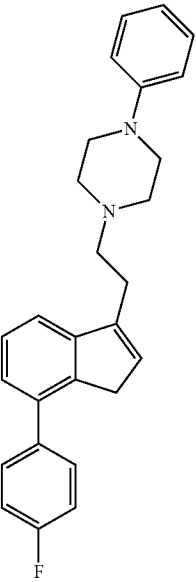 [SMILES: Fc1ccc(-c2cccc3c2CC=C3CCN2CCN(c3ccccc3)CC2)cc1] | A | 1-(2-(7-(4-Fluorophenyl)-1H-inden-3-yl)ethyl)-4-phenylpiperazine maleate | $^1$H-NMR (DMSO-d$_6$, 400 MHz) δ: 7.65 (m, 2H), 7.49 (dd, J = 7.8, 7.6 Hz, 1H), 7.45 (dd, J = 7.6, 7.6 Hz, 1H), 7.32-7.24 (m, 5H), 7.02 (d, J = 8 Hz, 2H), 6.86 (t, J = 7.2 Hz, 1H), 6.46 (s, 1H), 6.03 (s, 2H), 3.75 (m, 2H), 3.47 (s, 2H), 3.30 (m, 6H), 3.00 (m, 4H) ppm. |
| 15 | 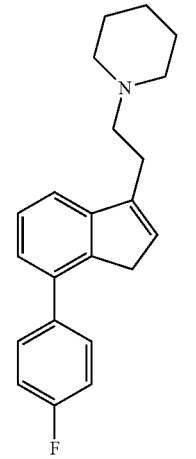 [SMILES: Fc1ccc(-c2cccc3c2CC=C3CCN2CCCCC2)cc1] | A | 1-(2-(7-(4-Fluorophenyl)-1H-inden-3-yl)ethyl)piperidine maleate | $^1$H-NMR (DMSO-d$_6$, 400 MHz) δ: 9.20 (s, 1H), 7.64 (m, 2H), 7.47 (dd, J = 7.4, 1.4 Hz, 1H), 7.44 (m, 1H), 7.31-7.26 (m, 3H), 6.45 (s, 1H), 6.04 (s, 2H), 3.57 (m, 2H), 3.46 (d, J = 1.2 Hz, 2H), 2.98 (m, 4H), 1.84 (m, 2H), 1.68 (m, 4H) ppm. |
| 16 | 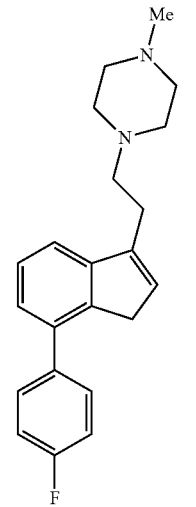 | A | 1-(2-(7-(4-Fluorophenyl)-1H-inden-3-yl)ethyl)-4-methylpiperazine maleate | $^1$H-NMR (DMSO-d$_6$, 400 MHz) δ: 7.63 (m, 2H), 7.41 (m, 2H), 7.29 (m, 2H), 7.22 (m, 1H), 6.38 (s, 1H), 6.12 (s, 2H), 3.41 (m, 2H), 3.30 (m, 8H), 2.86 (m, 2H), 2.78 (m, 2H), 2.69 (m, 3H) ppm. |

| Example | Structure | Method | Name | NMR |
|---|---|---|---|---|
| 17 | 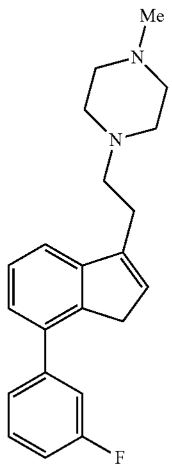 [SMILES: CN1CCN(CCC2=CCc3c2cccc3-c2cccc(F)c2)CC1] | A | 1-(2-(7-(3-Fluorophenyl)-1H-inden-3-yl)ethyl)-4-methylpiperazine maleate | $^1$H-NMR (DMSO-d$_6$, 400 MHz) δ: 7.50 (m, 1H), 7.45-7.40 (m, 4H), 7.27 (dd, J = 6.4, 2.4 Hz, 1H), 7.21 (m, 1H), 6.39 (s, 1H), 6.11 (s, 2H), 3.46 (s, 2H), 3.30 (m, 8H), 2.86 (m, 2H), 2.78 (m, 2H), 2.69 (s, 3H) ppm. |
| 18 | 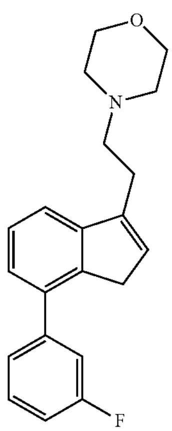 [SMILES: Fc1cccc(-c2cccc3c2CC=C3CCN2CCOCC2)c1] | A | 4-(2-(7-(3-Fluorophenyl)-1H-inden-3-yl)ethyl)morpholine maleate | $^1$H-NMR (DMSO-d$_6$, 400 MHz) δ: 7.52 (m, 1H), 7.48-7.32 (m, 4H), 7.30 (dd, J = 7.4, 1.4 Hz, 1H), 7.22 (tdd, J = 8.5, 2.1 Hz, 1H), 6.45 (s, 1H), 6.05 (s, 2H), 3.82 (m, 4H), 3.50 (s, 2H), 3.33 (m, 6H), 2.96 (m, 2H) ppm. |
| 19 | 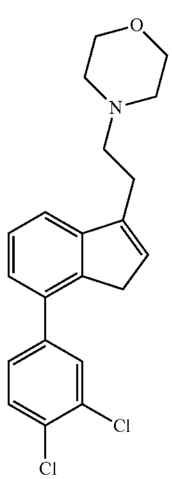 [SMILES: Clc1ccc(-c2cccc3c2CC=C3CCN2CCOCC2)cc1Cl] | A | 4-(2-(7-(3,4-Dichlorophenyl)-1H-inden-3-yl)ethyl)morpholine maleate | $^1$H-NMR (DMSO-d$_6$, 400 MHz) δ: 7.86 (d, J = 2 Hz, 1H), 7.72 (d, J = 8 Hz, 1H), 7.61 (dd, J = 8.2, 2.4 Hz, 1H), 7.51 (dd, J = 7.2, 1.2 Hz, 1H), 7.46 (t, J = 7.4 Hz, 1H), 7.31 (dd, J = 7.6 Hz, 1H), 6.46 (s, 1H), 6.05 (s, 2H), 3.76 (m, 4H), 3.49 (m, 2H), 3.31 (m, 6H), 2.95 (m, 2H) ppm. |

-continued

| Example | Structure | Method | Name | NMR |
|---|---|---|---|---|
| 20 | 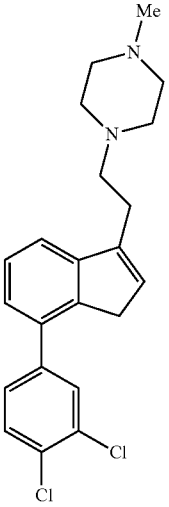 [SMILES: CN1CCN(CCC2=CCc3c2cccc3-c2ccc(Cl)c(Cl)c2)CC1] | A | 1-(2-(7-(3,4-Dichlorophenyl)-1H-inden-3-yl)ethyl)-4-methylpiperazine maleate | $^1$H-NMR (DMSO-d$_6$, 400 MHz) δ: 7.85 (d, J = 2.4 Hz, 1H), 7.71 (d, J = 7.2 Hz, 1H), 7.60 (dd, J = 8.2, 2.2 Hz, 1H), 7.46 (dd, J = 8, 2 Hz, 1H), 7.43 (d, J = 7.2 Hz, 1H), 7.28 (dd, J = 7.2, 1.6 Hz, 1H), 6.40 (s, 1H), 6.12 (s, 2H), 3.45 (s, 2H), 3.31 (m, 8H), 2.85 (m, 2H), 2.79 (m, 2H), 2.69 (s, 3H) ppm. |
| 21 | 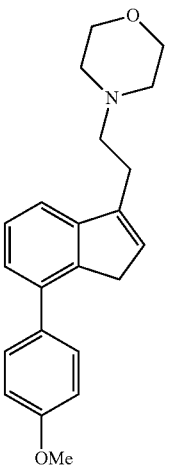 | A | 4-(2-(7-(4-Methoxyphenyl)-1H-inden-3-yl)ethyl)morpholine maleate | $^1$H-NMR (DMSO-d$_6$, 400 MHz) δ: 7.53 (d, J = 9.2 Hz, 2H), 7.42 (m, 2H), 7.23 (dd, J = 5.8, 2.6 Hz, 1H), 7.02 (d, J = 8.8 Hz, 2H), 6.43 (s, 1H), 6.05 (s, 2H), 3.80 (s, 3H), 3.70 (m, 2H), 3.45 (m, 2H), 3.31 (m, 8H), 2.95 (m, 2H) ppm. |
| 22 | 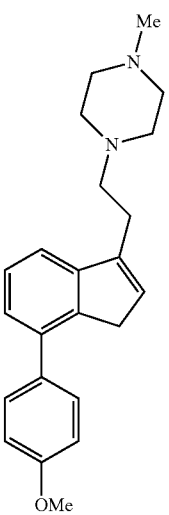 | A | 1-(2-(7-(4-Methoxyphenyl)-1H-inden-3-yl)ethyl)-4-methylpiperazine maleate | $^1$H-NMR (DMSO-d$_6$, 400 MHz) δ: 7.52 (d, J = 8.4 Hz, 2H), 7.37 (m, 2H), 7.20 (dd, J = 5.8, 2.6 Hz, 1H), 7.02 (d, J = 8.4 Hz, 2H), 6.37 (s, 1H), 6.12 (s, 2H), 3.79 (s, 3H), 3.41 (m, 2H), 3.25 (m, 8H), 2.87 (m, 2H), 2.78 (m, 2H), 2.67 (m, 3H) ppm. |

-continued

| Example | Structure | Method | Name | NMR |
|---|---|---|---|---|
| 23 | 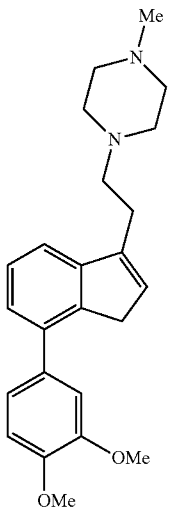 [SMILES: COc1ccc(-c2cccc3c2CC=C3CCN2CCN(C)CC2)cc1OC] | A | 1-(2-(7-(3,4-Dimethoxyphenyl)-1H-inden-3-yl)ethyl)-4-methylpiperazine maleate | ¹H-NMR (DMSO-$d_6$, 400 MHz) δ: 7.37 (m, 2H), 7.24 (dd, J = 5.6, 2.8 Hz, 1H), 7.14-7.10 (m, 2H), 7.02 (d, J = 8 Hz, 1H), 6.38 (s, 1H), 6.12 (s, 2H), 3.79 (m, 6H), 3.45 (s, 2H), 3.30 (m, 8H), 2.86 (m, 2H), 2.78 (m, 2H), 2.69 (m, 3H) ppm. |
| 24 | 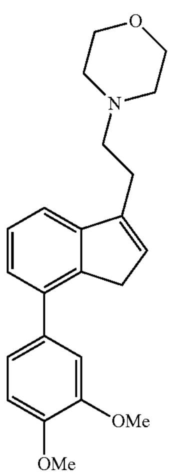 [SMILES: COc1ccc(-c2cccc3c2CC=C3CCN2CCOCC2)cc1OC] | A | 4-(2-(7-(3,4-Dimethoxyphenyl)-1H-inden-3-yl)ethyl)morpholine maleate | ¹H-NMR (DMSO-$d_6$, 400 MHz) δ: 7.42 (m, 2H), 7.28 (dd, J = 6.4, 2.4 Hz, 1H), 7.12 (m, 2H), 7.03 (d, J = 8 Hz, 1H), 6.44 (s, 1H), 6.10 (s, 2H), 3.80 (m, 6H), 3.49 (s, 2H), 3.41-3.20 (m, 10H), 2.97 (m, 2H) ppm. |
| 25 | 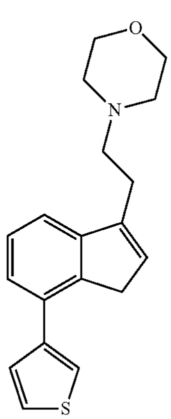 [SMILES: C1=C(CCN2CCOCC2)c2cccc(-c3ccsc3)c2C1] | A | 4-(2-(7-(Thiophen-3-yl)-1H-inden-3-yl)ethyl)morpholine maleate | ¹H-NMR (DMSO-$d_6$, 400 MHz) δ: 7.87 (dd, J = 3, 1.4 Hz, 1H), 7.67 (dd, J = 5.3 Hz, 1H), 7.56 (dd, J = 4.8, 1.6 Hz, 1H), 7.46 (dd, J = 6.2, 2.6 Hz, 1H), 7.42 (m, 2H), 6.47 (s, 1H), 6.04 (s, 2H), 3.73 (m, 4H), 3.57 (m, 2H), 3.31 (m, 6H), 2.95 (m, 2H) ppm. |

| Example | Structure | Method | Name | NMR |
|---|---|---|---|---|
| 26 | 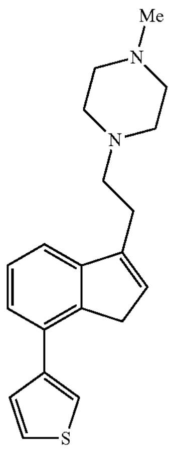 [SMILES: CN1CCN(CCC2=CCc3c2cccc3-c2ccsc2)CC1] | A | 1-Methyl-4-(2-(7-(thiophen-3-yl)-1H-inden-3-yl)ethyl)piperazine maleate | $^1$H-NMR (DMSO-$d_6$, 400 MHz) δ: 7.85 (dd, J = 3.4, 1.4 Hz, 1H), 7.66 (dd, J = 4.8, 2.8 Hz, 1H), 7.55 (dd, J = 5.2, 1.6 Hz, 1H), 7.43 (m, 1H), 7.38 (m, 2H), 6.41 (s, 1H), 6.12 (m, 2H), 3.52 (s, 2H), 3.32 (m, 8H), 2.87 (m, 2H), 2.78 (m, 2H), 2.68 (m, 3H) ppm. |
| 27 | 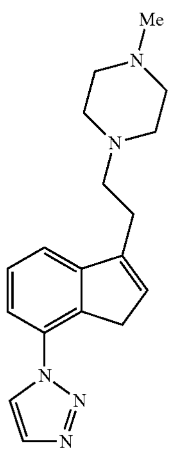 [SMILES: CN1CCN(CCC2=CCc3c2cccc3-n2ccnn2)CC1] | A | 1-(2-(7-(1H-1,2,3-Triazol-1-yl)-1H-inden-3-yl)ethyl)-4-methylpiperazine maleate | $^1$H-NMR (DMSO-$d_6$, 400 MHz) δ: 8.79 (s, 1H), 8.00 (s, 1H), 7.56 (m, 3H), 6.48 (s, 1H), 6.12 (s, 2H), 3.61 (s, 2H), 2.31 (m, 8H), 2.81 (m, 4H), 2.70 (s, 3H) ppm. |
| 28 | 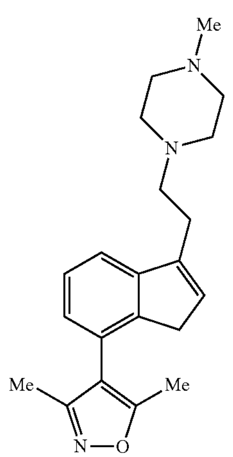 [SMILES: Cc1noc(C)c1-c1cccc2c1CC=C2CCN1CCN(C)CC1] | B | 3,5-Dimethyl-4-(3-(2-(4-methylpiperazine-1-yl)ethyl)-1H-inden-7-yl)isoxazole maleate | $^1$H-NMR (DMSO-$d_6$, 400 MHz) δ: 7.46 (dd, J = 7.2, 0.8 Hz, 1H), 7.40 (t, J = 7.4 Hz, 1H), 7.08 (dd, J = 7.2, 1 Hz, 1H), 6.39 (s, 1H), 6.12 (s, 2H), 3.32 (m, 6H), 3.12 (s, 2H), 2.85 (m, 4H), 2.77 (m, 2H), 2.69 (m, 3H), 2.28 (s, 3H), 2.04 (s, 3H) ppm. |

-continued

| Example | Structure | Method | Name | NMR |
|---|---|---|---|---|
| 29 | 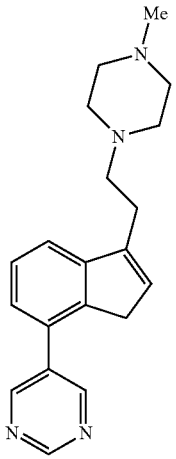 [SMILES: CN1CCN(CCC2=CCc3c2cccc3-c2cncnc2)CC1] | B | 5-(3-(2-(4-Methylpiperazin-1-yl)ethyl)-1H-inden-7-yl)pyrimidine maleate | $^1$H-NMR (DMSO-$d_6$, 400 MHz) δ: 9.22 (s, 1H), 9.10 (s, 2H), 7.50 (m, 2H), 7.37 (dd, J = 7.1, 2.6 Hz, 1H), 6.43 (s, 1H), 6.12 (s, 2H), 3.52 (s, 2H), 3.26 (m, 8H), 2.80 (m, 4H), 2.68 (s, 3H) ppm. |
| 30 | 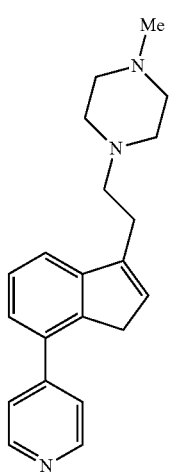 [SMILES: CN1CCN(CCC2=CCc3c2cccc3-c2ccncc2)CC1] | A | 1-Methyl-4-(2-(7-(pyridin-4-yl)-1H-inden-3-yl)ethyl)piperazine maleate | $^1$H-NMR (DMSO-$d_6$, 400 MHz) δ: 8.65 (d, J = 4.8 Hz, 2H), 7.65 (d, J = 4.4 Hz, 2H), 7.49 (m, 2H), 7.35 (dd, J = 7.2, 1.6 Hz, 1H), 6.42 (s, 1H), 6.12 (s, 2H), 3.51 (s, 2H), 3.29 (m, 8H), 2.86 (m, 2H), 2.80 (m, 2H), 2.69 (s, 3H) ppm. |
| 31 | 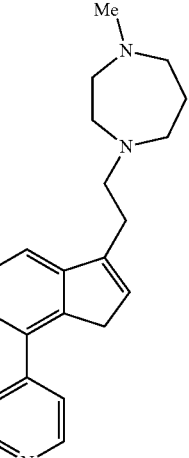 | A | 1-Methyl-4-(2-(7-(pyridin-4-yl)-1H-inden-3-yl)ethyl)-1,4-diazepane maleate | $^1$H-NMR (DMSO-$d_6$, 300 MHz) δ: 7.87 (d, J = 4.5 Hz, 2H), 7.65 (d, J = 4.8 Hz, 2H), 7.56 (d, J = 7.2 Hz, 1H), 7.49 (t, J = 7.5 Hz, 1H), 7.37 (d, J = 7.8 Hz, 1H), 6.46 (s, 1H), 6.13 (s, 2H), 3.54 (m, 6H), 3.32 (m, 6H), 2.96 (m, 2H), 2.80 (s, 3H), 2.10 (m, 2H) ppm. |

| Example | Structure | Method | Name | NMR |
|---|---|---|---|---|
| 32 | 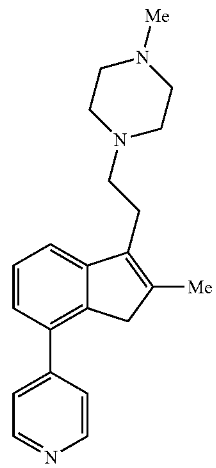 [SMILES: CC1=C(CCN2CCN(C)CC2)c2cccc(-c3ccncc3)c2C1] | A | 1-Methyl-4-(2-(2-methyl-7-(pyridin-4-yl)-1H-inden-3-yl)ethyl)piperazine maleate | ¹H-NMR (DMSO-d₆, 400 MHz) δ: 8.65 (d, J = 5.6 Hz, 2H), 7.63 (d, J = 6.4 Hz, 2H), 7.41 (t, J = 7.4 Hz, 1H), 7.35 (dd, J = 7, 1.2 Hz, 1H), 7.25 (dd, J = 7.2, 1.2 Hz, 1H), 6.15 (s, 2H), 3.48 (s, 2H), 3.10 (m, 6H), 2.72-2.54 (m, 9H), 2.06 (s, 3H) ppm. |
| 33 | 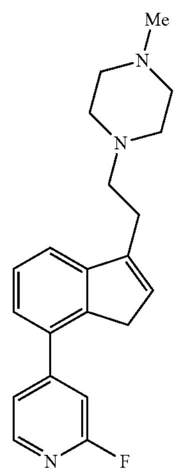 [SMILES: CN1CCN(CCC2=CCc3c2cccc3-c2ccnc(F)c2)CC1] | B | 1-(2-(7-(2-Fluoropyridin-4-yl)-1H-inden-3-yl)ethyl)-4-methylpiperazine maleate | ¹H-NMR (DMSO-d₆, 400 MHz) δ: 8.69 (d, J = 1.6 Hz, 1H), 8.52 (d, J = 4 Hz, 1H), 7.61 (dd, J = 6.6, 5 Hz, 1H), 7.53 (d, J = 7.2 Hz, 1H), 7.47 (t, J = 7.6 Hz, 1H), 7.26 (d, J = 7.6 Hz, 1H), 6.40 (s, 1H), 6.11 (s, 2H), 3.29 (m, 10 H), 2.85 (m, 2H), 2.80 (m, 2H), 2.69 (s, 3H) ppm. |
| 34 | 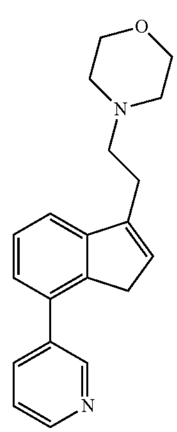 [SMILES: C1=C(CCN2CCOCC2)c2cccc(-c3cccnc3)c2C1] | A | 4-(2-(7-(Pyridin-3-yl)-1H-inden-3-yl)ethyl)morpholine maleate | ¹H-NMR (DMSO-d₆, 400 MHz) δ: 8.82 (d, J = 2 Hz, 1H), 8.59 (dd, J = 4.6, 1.4 Hz, 1H), 8.04 (dt, J = 6, 2 Hz, 1H), 7.51 (m, 3H), 7.33 (dd, J = 7.2, 1.2 Hz, 1H), 6.47 (s, 1H), 6.07 (s, 2H), 3.82 (m, 4H), 3.51 (s, 2H), 3.40 (m, 2H), 3.29 (m, 2H), 2.97 (m, 2H) ppm. |

-continued

| Example | Structure | Method | Name | NMR |
|---|---|---|---|---|
| 35 | 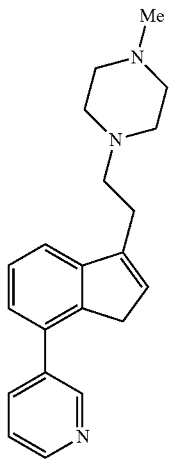 [SMILES: CN1CCN(CCC2=CCc3c2cccc3-c2cccnc2)CC1] | A | 1-Methyl-4-(2-(7-(pyridin-3-yl)-1H-inden-3-yl)ethyl)piperazine maleate | $^1$H-NMR (DMSO-d$_6$, 400 MHz) δ: 8.81 (d, J = 1.6 Hz, 1H), 8.59 (dd, J = 4.8, 1.6 Hz, 1H), 8.04 (dt, J = 8, 2 Hz, 1H), 7.50 (dd, J = 8, 4.8 Hz, 1H), 7.46 (m, 2H), 7.29 (dd, J = 6, 2.4 Hz, 1H), 6.41 (s, 1H), 6.12 (s, 2H), 3.46 (s, 2H), 3.10 (m, 8H), 2.86 (m, 2H), 2.79 (m, 2H), 2.70 (m, 3H) ppm. |
| 36 | 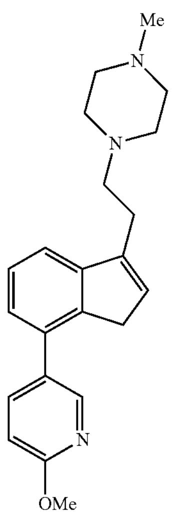 [SMILES: COc1ccc(-c2cccc3c2CC=C3CCN2CCN(C)CC2)cn1] | B | 1-(2-(7-(6-Methoxypyridin-3-yl)-1H-inden-3-yl)ethyl)-4-methylpiperazine maleate | $^1$H-NMR (DMSO-d$_6$, 400 MHz) δ: 8.40 (d, J = 2 Hz, 1H), 7.96 (dd, J = 8.6, 1.8 Hz, 1H), 7.42 (m, 2H), 7.25 (m, 1H), 6.91 (d, J = 8.8 Hz, 1H), 6.39 (s, 1H), 6.12 (s, 2H), 3.89 (s, 3H), 3.44 (s, 2H), 3.14 (m, 8H), 2.86 (m, 2H), 2.79 (m, 2H), 2.69 (s, 3H) ppm. |
| 37 | 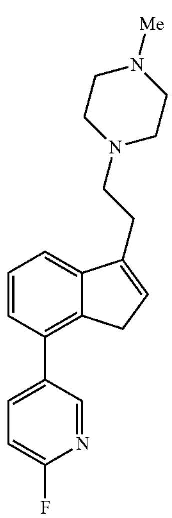 [SMILES: CN1CCN(CCC2=CCc3c2cccc3-c2ccc(F)nc2)CC1] | B | 1-(2-(7-(6-Fluoropyridin-3-yl)-1H-inden-3-yl)ethyl)-4-methylpiperazine maleate | $^1$H-NMR (DMSO-d$_6$, 400 MHz) δ: 8.47 (d, J = 2.8 Hz, 1H), 8.24 (dt, J = 8.4, 2.7 Hz, 1H), 7.46 (m, 2H), 7.28 (m, 2H), 6.41 (s, 1H), 6.12 (s, 2H), 3.46 (s, 2H), 3.11 (m, 8H), 2.86 (m, 2H), 2.79 (m, 2H), 2.69 (m, 3H) ppm. |

-continued

| Example | Structure | Method | Name | NMR |
|---|---|---|---|---|
| 38 | 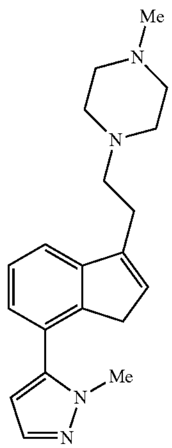 [SMILES: CN1CCN(CCC2=CCc3c2cccc3-c2ccnn2C)CC1] | B | 1-Methyl-4-(2-(7-(1-methyl-1H-pyrazol-5-yl)-1H-inden-3-yl)ethyl)piperazine maleate | $^1$H-NMR (DMSO-d$_6$, 400 MHz) δ: 7.51 (d, J = 2 Hz, 1H), 7.48 (d, J = 6.8 Hz, 1H), 7.44 (t, J = 7.4 Hz, 1H), 7.26 (d, J = 6.8 Hz, 1H), 6.49 (d, J = 2 Hz, 1H), 6.39 (s, 1H), 6.12 (s, 2H), 3.72 (s, 3H), 3.29 (m, 8H), 2.84 (m, 4H), 2.78 (m, 2H), 2.69 (s, 3H) ppm. |
| 39 | 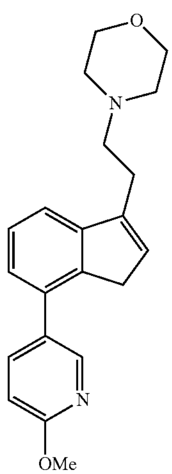 [SMILES: COc1ccc(-c2cccc3c2CC=C3CCN2CCOCC2)cn1] | B | 4-(2-(7-(6-Methoxypyridin-3-yl)-1H-inden-3-yl)ethyl)morpholine maleate | $^1$H-NMR (DMSO-d$_6$, 300 MHz) δ: 8.40 (d, J = 2.4 Hz, 1H), 7.96 (dd, J = 8.7, 2.4 Hz, 1H), 7.46 (m, 2H), 7.27 (dd, J = 6.6, 2.1 Hz, 1H), 6.92 (d, J = 8.4 Hz, 1H), 6.45 (s, 1H), 6.04 (s, 2H), 3.90 (s, 3H), 3.80 (m, 4H), 3.47 (d, J = 1.2 Hz, 2H), 3.30 (m, 6H), 2.94 (m, 2H) ppm. |
| 40 | 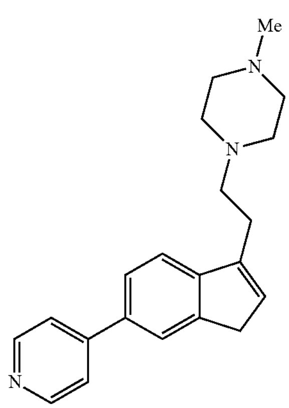 [SMILES: CN1CCN(CCC2=CCc3cc(-c4ccncc4)ccc32)CC1] | A | 1-Methyl-4-(2-(6-pyridin-4-yl)-1H-inden-3-yl)ethyl)piperazine maleate | $^1$H-NMR (DMSO-d$_6$, 400 MHz) δ: 8.62 (d, J = 6 Hz, 1H), 7.93 (s, 1H), 7.76-7.74 (m, 3H), 7.53 (d, J = 8.4 Hz, 1H), 6.46 (s, 1H), 6.12 (s, 2H), 3.44 (s, 2H), 3.31 (m, 8H), 2.80 (m, 2H), 2.79 (m, 2H), 2.69 (s, 3H) ppm. |

| Example | Structure | Method | Name | NMR |
|---|---|---|---|---|
| 41 | (structure) | A | 1-(2-(6-(2-Fluoropyridin-4-yl)-1H-inden-3-yl)ethyl)-4-methylpiperazine maleate | $^1$H-NMR (DMSO-$d_6$, 300 MHz) δ: 8.64 (d, J = 2.7 Hz, 1H), 8.49 (d, J = 4.5 Hz, 1H), 7.78 (s, 1H), 7.63 (m, 2H), 7.55 (d, J = 7.8 Hz, 1H), 6.48 (s, 1H), 6.13 (s, 2H), 3.44 (s, 2H), 3.19 (m, 8H), 2.84 (m, 2H), 2.80 (m, 2H), 2.69 (s, 3H) ppm. |

Biological Activity
Pharmacological Study

Brain membrane preparation and binding assays for the σ1-receptor were performed as described (DeHaven-Hudkins, D. L., L. C. Fleissner, and F. Y. Ford-Rice, 1992, Characterization of the binding of [$^3$H](+)pentazocine to 6 recognition sites in guinea pig brain, Eur. J. Pharmacol. 227, 371-378) with some modifications. Guinea pig brains were homogenized in 10 vols. (w/v) of Tris-HCl 50 mM 0.32 M sucrose, pH 7.4, with a Kinematica Polytron PT 3000 at 15000 r.p.m. for 30 s. The homogenate was centrifuged at 1000 g for 10 min at 4° C. and the supernatants collected and centrifuged again at 48000 g for 15 min at 4° C. The pellet was resuspended in 10 volumes of Tris-HCl buffer (50 mM, pH 7.4), incubated at 37° C. for 30 min, and centrifuged at 48000 g for 20 min at 4° C. Following this, the pellet was re-suspended in fresh Tris-HCl buffer (50 mM, pH 7.4) and stored on ice until use.

The radioligand used was [$^3$H]-(+)-pentazocine at 5.0 nM and the final volume was 200 μl. The incubation was initiated with the addition of 100 μl of membrane at a final tissue concentration of approximately 5 mg tissue net weight/mL and the incubation time was 150 m. at 37° C. After incubation, the membranes were collected onto pre-treated glass fiber filterplate (MultiScreen-FC, Millipore), with polyethylenimine 0.1%. The filters were washed two times with 200 μl of washing buffer (50 mM Tris Cl, pH=7.4) and then 25 μl of Ecoscint H liquid scintillation cocktail were added. Microplates were allowed to set for several hours and then quantified by liquid scintillation spectrophotometry (1450 Microbeta, Wallac). Nonspecific binding was determined with 1 μM haloperidol.

Some of the results obtained are shown in table (I).

TABLE (I)

| Compound | $K_i$ σ1 (nM) |
|---|---|
| 1 | 3 |
| 2 | 12 |
| 3 | 47 |
| 4 | 24 |
| 5 | 13 |
| 6 | 31 |
| 7 | 63 |
| 8 | 7 |
| 9 | 7 |
| 10 | 13 |
| 11 | 28 |
| 12 | 51 |
| 13 | 4 |
| 14 | 24 |
| 15 | 8 |
| 16 | 12 |
| 17 | 14 |
| 18 | 4 |
| 19 | 12 |
| 20 | 25 |
| 21 | 53 |
| 22 | 129 |
| 25 | 6 |
| 26 | 7 |
| 27 | 185 |
| 28 | 36 |
| 29 | 168 |
| 30 | 26 |
| 31 | 29 |
| 33 | 29 |
| 34 | 82 |
| 35 | 61 |
| 36 | 37 |
| 37 | 34 |
| 38 | 30 |
| 39 | 180 |
| 40 | 143 |
| 41 | 120 |

The invention claimed is:

1. A compound of formula (I):

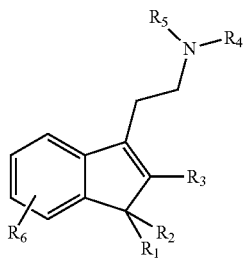

(I)

wherein
R$_1$, R$_2$ and R$_3$ are independently selected from hydrogen and a branched or unbranched, saturated or unsaturated, C$_{1-10}$ aliphatic radical, wherein the aliphatic radical may be optionally substituted by one or more substituents selected from the group consisting of a C$_{1-6}$ alkyl group, a C$_{3-9}$ cycloalkyl group, a linear or branched C$_{1-6}$ alkoxy group, —F, —Cl, —I, —Br, —CF$_3$, —CH$_2$F, —CHF$_2$, —CN, —OH, —SH, —NH$_2$, oxo, —(C=O)R', —SR', —SOR', —SO$_2$R', —NHR', and —NR'R" wherein each R' and R" independently represents a linear or branched C$_{1-6}$-alkyl group, with the proviso that R$_1$ and R$_2$ are always identical;
R$_4$ and R$_5$ together with the bridging nitrogen form a C$_{3-9}$ heterocycloalkyl, optionally having at least one additional heteroatom as a ring member and optionally substituted by a branched or unbranched, saturated or unsaturated C$_{1-10}$ aliphatic radical or by an aryl group optionally monosubstituted by a C$_{1-6}$ alkyl or a halogen; and
R$_6$ is a (5-6)-membered aryl or (5-6)-membered heteroaryl radical optionally substituted by one or more substituents independently selected from the group consisting of a C$_{1-6}$ alkyl group, a linear or branched C$_{1-6}$ alkoxy group, a phenyl group, wherein the phenyl group may be optionally substituted by one or more substituents selected from the group consisting of a C$_{1-6}$ alkyl group, a linear or branched C$_{1-6}$ alkoxy group, —F, —Cl, —I, —Br, —CF$_3$, —CH$_2$F, —CHF$_2$, —CN, —OH, —SH, —NH$_2$, —(C=O)R', —SR', —SOR', —SO$_2$R', —N(C=O) OR',—NHR', and —NR'R" wherein each R' and R" independently represents a linear or branched C$_{1-6}$-alkyl group, —F, —Cl, —I, —Br, —CF$_3$, —CH$_2$F, —CHF$_2$, —CN, —OH, —SH, —NH$_2$, —(C=O)R', —SR', —SOR', —SO$_2$R', —N(C=O) OR',—NHR', and —NR'R" wherein each R' and R" independently represents a linear or branched C$_{1-6}$-alkyl group;
or a pharmaceutically acceptable salt, stereoisomer or tautomer thereof.

2. The compound according to claim 1, wherein R$_1$, R$_2$ and R$_3$ are independently hydrogen or C$_{1-6}$ alkyl.

3. The compound according to claim 1, wherein R$_4$ and R$_5$ together with the bridging nitrogen form a group selected from the group consisting of:

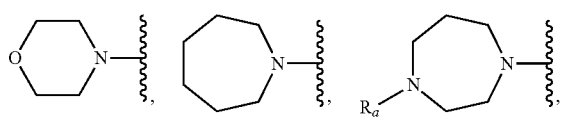

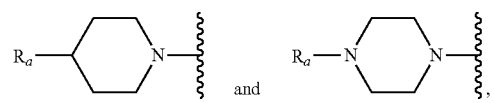

wherein each R$_a$ is independently selected from hydrogen, a C$_{1-6}$ alkyl or a phenyl group optionally substituted by a halogen.

4. The compound according to claim 1, wherein R$_6$ is a group selected from the group consisting of:

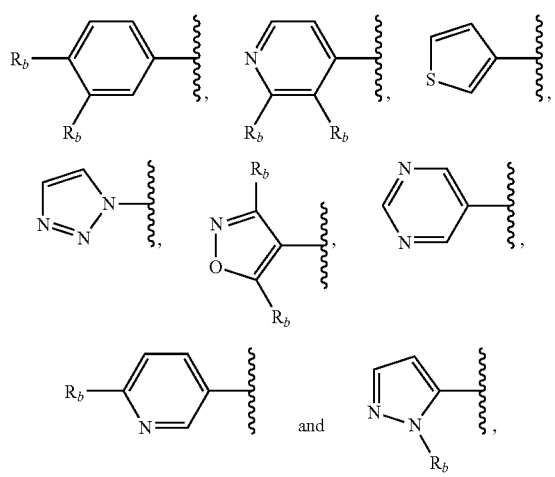

wherein each R$_b$ is independently selected from hydrogen, a C$_{1-6}$ alkyl group, —F, —Cl, —I, —Br and a linear or branched C$_{1-6}$ alkoxy group.

5. The compound according to claim 1, wherein R$_1$, R$_2$ and R$_3$ are independently hydrogen or C$_{1-6}$ alkyl;

R$_4$ and R$_5$ together with the bridging nitrogen form a group selected from the group consisting of:

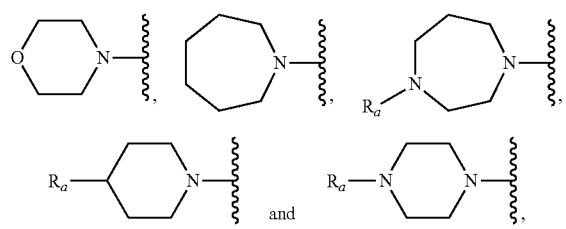

wherein each R$_a$ is independently selected from hydrogen, a C$_{1-6}$ alkyl and a phenyl group optionally substituted by a halogen; and R$_6$ is a group selected from the group consisting of:

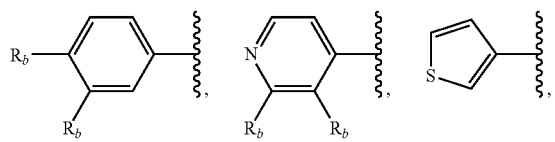

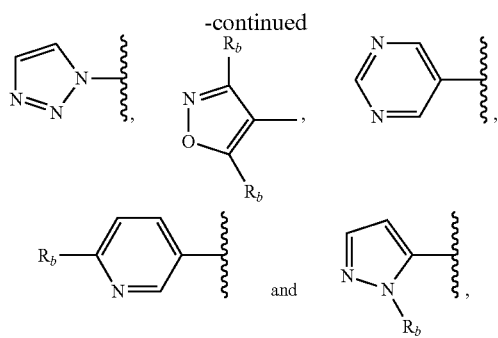

wherein each $R_b$ is independently selected from hydrogen, a $C_{1-6}$ alkyl group, —F, —Cl, —I, —Br and a linear or branched $C_{1-6}$ alkoxy group.

6. The compound according to claim 1, which is selected from the group consisting of:

[1] 4-(2-(7-phenyl-1H-inden-3-yl)ethyl)morpholine maleate,
[2] 1-(2-(7-(4-fluorophenyl)-1H-inden-3-yl)ethyl)azepane hydrochloride,
[3] 4-(2-(7-(pyridin-4-yl)-1H-inden-3-yl)ethyl)morpholine maleate,
[4] 1-(2-(7-(3-fluoropyridin-4-yl)-1H-inden-3-yl)ethyl)-4-methylpiperazine maleate,
[5] 1-methyl-4-(2-(7-phenyl-1H-inden-3-yl)ethyl)piperazine maleate,
[6] 1-phenyl-4-(2-(7-phenyl-1H-inden-3-yl)ethyl)piperazine maleate,
[7] 1-(3-chlorophenyl)-4-(2-(7-phenyl-1H-inden-3-yl)ethy)piperazine maleate,
[8] 1-(2-(7-phenyl-1 H-inden-3-yl)ethy)piperidine maleate,
[9] 1-(2-(7-phenyl-1H-inden-3-yl)ethy)azepane maleate,
[10] 4-phenyl-1-(2-(7-phenyl-1H-inden-3)ethy)piperidine maleate,
[11] 4-(2-(2-methyl-7-phenyl-1H-inden-3-yl)ethyl)morpholine maleate,
[12] 1-methyl-4-(2-(2-methyl-7-phenyl-1H-inden-3-yl)ethyl)piperazine maleate,
[13] 4-(2-(7-(4-fluorophenyl)-1H-inden-3-yl)ethyl)morpholine maleate,
[14] 1-(2-(7-(4-fluorophenyl)-1H-inden-3-Yl)pethyl)-4-phenylpiperazine maleate,
[15] 1-(2-(7-(4-fluorophenyl)-1H-inden-3-yl)ethyl)piperidine maleate,
[16] 1-(2-(7-(4-fluorophenyl)-1H-inden-3-yl)ethyl)-4-methylpiperazine maleate,
[17] 1-(2-(7-(3-fluorophenyl)-1H-inden-3-yl)pethyl)-4-methylpiperazine maleate,
[18] 4-(2-(7-(3-fluorophenyl)-1H-inden-3-yl)ethyl)morpholine maleate,
[19] 4-(2-(7-(3,4-dichlorophenyl)-1H-inden-3-yl)ethyl)morpholine maleate,
[20] 1-(2-(7-(3,4-dichlorophenyl)-1H-inden-3-yl)pethyl)-4-methylpiperazine maleate,
[21] 4-(2-(7-(4-methoxyphenyl)-1H-inden-3-yl)pethyl)morpholine maleate,
[22] 1-(2-(7-(4-methoxyphenyl)-1H-inden-3-yl)pethyl)-4-methylpiperazine maleate,
[23] 1-(2-(7-(3,4-dimethoxyphenyl)-1H-inden-3-yl)pethyl)-4-methylpiperazine maleate,
[24] 4-(2-(7-(3,4-dimethoxyphenyl)-1H-inden-3-yl)ethyl)morpholine maleate,
[25] 4-(2-(7-(thiophen-3-yl)-1H-inden-3-yl)ethyl)morpholine maleate,
[26] 1-methyl-4-(2-(7-(thiophen-3-yl)-1H-inden-3-yl)ethyl)piperazine maleate,
[27] 1-(2-(7-(1H-1,2,3-triazol-1-yl)-1H-inden-3-yl)ethyl)-4-methylpiperazine maleate,
[28] 3,5-dimethyl-4-(3-(2-(4-methylpiperazin-1-yl)pethyl)-1H-inden-7-yl)isoxazole maleate,
[29] 5-(3-(2-(4-methylpiperazin-1-yl)ethyl)-1H-inden-7-yl)pyrimidine maleate,
[30] 1-methyl-4-(2-(7-(pyridin-4-yl)-1H-inden-3-yl)pethyl)piperazine maleate,
[31] 1-methyl-4-(2-(7-(pyridin-4-yl)-1H-inden-3-yl)ethyl)-1,4-diazepane maleate,
[32] 1-methyl-4-(2-(2-methyl-7-(pyridin-4-yl)-1H-inden-3-yl)ethyl)piperazine maleate,
[33] 1-(2-(7-(2-fluoropyridin-4-yl)-1H-inden-3-yl)ethyl)-4-methylpiperazine maleate,
[34] 4-(2-(7-(pyridin-3-yl)-1H-inden-3-yl)ethyl)morpholine maleate,
[35] 1-methyl-4-(2-(7-(pyridin-3-yl)-1H-inden-3-yl)ethyl)piperazine maleate,
[36] 1-(2-(7-(6-methoxypyridin-3-yl)-1H-inden-3-yl)ethyl)-4-methylpiperazine maleate,
[37] 1-(2-(7-(6-fluoropyridin-3-yl)-1H-inden-3-yl)ethyl)-4-methylpiperazine maleate,
[38] 1-methyl-4-(2-(7-(1-methyl-1H-pyrazol-5-yl)-1H-inden-3-yl)ethyl)piperazine maleate,
[39] 4-(2-(7-(6-methoxypyridin-3-yl)-1H-inden-3-yl)ethyl)morpholine maleate,
[40] 1-methyl-4-(2-(6-pyridin-4-yl)-1H-inden-3-yl)pethyl)piperazine maleate,
[41] 1-(2-(6-(2-fluoropyridin-4-yl)-1H-inden-3-yl)ethyl)-4-methylpiperazine maleate, and pharmaceutically acceptable salts thereof.

7. A pharmaceutical composition comprising a compound according to claim 1 and at least a pharmaceutically acceptable carrier, additive, adjuvant or vehicle.

8. A process for the preparation of a compound of formula (I):

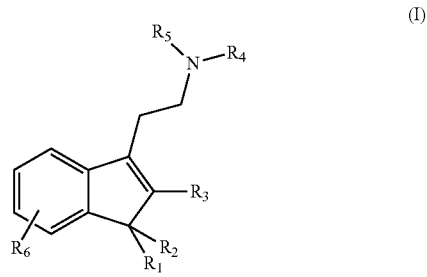

wherein $R_1$, $R_2$ and $R_3$ are independently selected from hydrogen and a branched or unbranched, saturated or unsaturated, $C_{1-10}$ aliphatic radical, wherein the aliphatic radical may be optionally substituted by one or more substituents selected from the group consisting of a $C_{1-6}$ alkyl group, a $C_{3-9}$ cycloalkyl group, a linear or branched $C_{1-6}$ alkoxy group, —F, —Cl, —I, —Br, —CF$_3$, —CH$_2$F, —CHF$_2$, —CN, —OH, —SH, —NH$_2$, oxo, —(C=O)R', —SR', —SOR', —SO$_2$R', —NHR', and —NR'R" wherein each R' and R" independently represents a linear or branched $C_{1-6}$-alkyl group, with the proviso that $R_1$ and $R_2$ are always identical;

$R_4$ and $R_5$ together with the bridging nitrogen form a $C_{3-9}$ heterocycloalkyl, optionally having at least one additional heteroatom as a ring member and optionally substituted by a branched or unbranched, saturated or unsaturated $C_{1-10}$ aliphatic radical or by an aryl group optionally monosubstituted by a $C_{1-6}$ alkyl or a halogen; and $R_6$ is a (5-6)-membered aryl or (5-6)-membered heteroaryl radical optionally substituted by one or more substituents independently selected from the group consisting of a $C_{1-6}$ alkyl group, a linear or branched $C_{1-6}$ alkoxy group, a phenyl group, wherein the phenyl group may be optionally substituted by one or more substituents selected from the group consisting of a $C_{1-6}$ alkyl group, a linear or branched $C_{1-6}$ alkoxy group, —F, —Cl, —I, —Br, —$CF_3$, —$CH_2F$, —$CHF_2$, —CN, —OH, —SH, —$NH_2$, —(C═O)R', —SR', —SOR', —$SO_2$R', —N(C═O) OR',—NHR', and —NR'R" wherein each R' and R" independently represents a linear or branched $C_{1-6}$-alkyl group, —F, —Cl, —I, —Br, —$CF_3$, —$CH_2F$, —$CHF_2$, —CN, —OH, —SH, —$NH_2$, —(C═O)R', —SR', —SOR', —$SO_2$R', —N(C═O) OR',—NHR', and —NR'R" wherein each R' and R" independently represents a linear or branched $C_{1-6}$-alkyl group;

the process comprising reaction between a compound of formula (II):

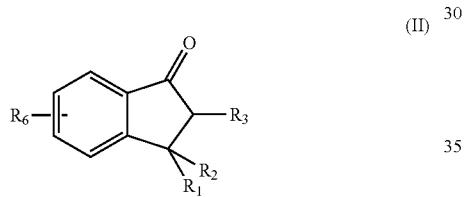

(II)

wherein $R_1$, $R_2$ and $R_3$ are independently selected from hydrogen and a branched or unbranched, saturated or unsaturated, $C_{1-10}$ aliphatic radical, wherein the aliphatic radical may be optionally substituted by one or more substituents selected from the group consisting of a $C_{1-6}$ alkyl group, a $C_{3-9}$ cycloalkyl group, a linear or branched $C_{1-6}$ alkoxy group, —F, —Cl, —I, —Br, —$CF_3$, —$CH_2F$, —$CHF_2$, —CN, —OH, —SH, —$NH_2$, oxo, —(C═O)R', —SR', —SOR', —$SO_2$R', —NHR', and —NR'R" wherein each R' and R" independently represents a linear or branched $C_{1-6}$-alkyl group, with the proviso that $R_1$ and $R_2$ are always identical; and $R_6$ is a (5-6)-membered aryl or (5-6)-membered heteroaryl radical optionally substituted by one or more substituents independently selected from the group consisting of a $C_1$ alkyl group, a linear or branched $C_{1-6}$ alkoxy group, a phenyl group, wherein the phenyl group may be optionally substituted by one or more substituents selected from the group consisting of a $C_{1-6}$ alkyl group, a linear or branched $C_{1-6}$ alkoxy group, —F, —Cl, —I, —Br, —$CF_3$, —$CH_2F$, —$CHF_2$, —CN, —OH, —SH, —$NH_2$, —(C═O)R', —SR', —SOR', —$SO_2$R', —N(C═O) OR',—NHR', and —NR'R" wherein each R' and R" independently represents a linear or branched $C_{1-6}$-alkyl group, —F, —Cl, —I, —Br, —$CF_3$, —$CH_2F$, —$CHF_2$, —CN, —OH, —SH, —$NH_2$, —(C═O)R', —SR', —SOR', —$SO_2$R', —N(C═O) OR',—NHR', and —NR'R"

wherein each R' and R" independently represents a linear or branched $C_{1-6}$-alkyl group;

and a compound of formula (III):

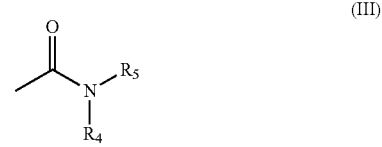

(III)

wherein $R_4$ and $R_5$ together with the bridging nitrogen form a $C_{3-9}$ heterocycloalkyl, optionally having at least one additional heteroatom as a ring member and optionally substituted by a branched or unbranched, saturated or unsaturated $C_{1-10}$ aliphatic radical or by an aryl group optionally monosubstituted by a $C_{1-6}$ alkyl or a halogen;

in the presence of a base in an inert solvent, followed by a reduction in the presence of a protic acid and a dehydrating agent, wherein the dehydrating agent is selected from the group consisting of trifluoroacetic acid, aqueous $H_2SO_4$, p-toluenesulfonic acid and aqueous solutions of $H_2SO_4$ and acetic acid.

9. A process for the preparation of a compound of formula (I):

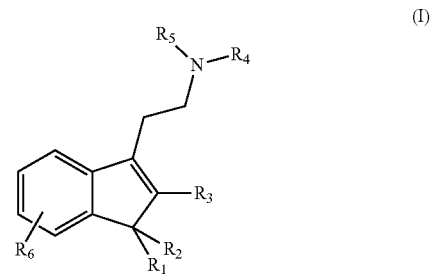

(I)

wherein $R_1$, $R_2$ and $R_3$ are independently selected from hydrogen and a branched or unbranched, saturated or unsaturated, $C_{1-10}$ aliphatic radical, wherein the aliphatic radical may be optionally substituted by one or more substituents selected from the group consisting of a $C_{1-6}$ alkyl group, a $C_{3-9}$ cycloalkyl group, a linear or branched $C_{1-6}$ alkoxy group, —F, —Cl, —I, —Br, —$CF_3$, —$CH_2F$, —$CHF_2$, —CN, —OH, —SH, —$NH_2$, oxo, —(C═O)R', —SR', —SOR', —$SO_2$R', —NHR', and —NR'R" wherein each R' and R" independently represents a linear or branched $C_{1-6}$-alkyl group, with the proviso that $R_1$ and $R_2$ are always identical;

$R_4$ and $R_5$ together with the bridging nitrogen form a $C_{3-9}$ heterocycloalkyl, optionally having at least one additional heteroatom as a ring member and optionally substituted by a branched or unbranched, saturated or unsaturated $C_{1-10}$ aliphatic radical or by an aryl group optionally monosubstituted by a $C_{1-6}$ alkyl or a halogen; and $R_6$ is a (5-6)-membered aryl or (5-6)-membered heteroaryl radical optionally substituted by one or more substituents independently selected from the group consisting of a $C_{1-6}$ alkyl group, a linear or branched $C_{1-6}$ alkoxy group, a phenyl group, wherein the phenyl group may be optionally substituted by one or more substituents selected from the group consisting of a $C_{1-6}$ alkyl group, a linear or branched $C_{1-6}$ alkoxy group, —F, —Cl, —I, —Br, —$CF_3$, —$CH_2F$, —$CHF_2$, —CN, —OH, —SH, —$NH_2$, —(C=O)R', —SR', —SOR', —$SO_2R'$, —N(C=O) OR',—NHR', and —NR'R" wherein each R' and R" independently represents a linear or branched $C_{1-6}$-alkyl group, —F, —Cl, —I, —Br, —$CF_3$, —$CH_2F$, —$CHF_2$, —CN, —OH, —SH, —$NH_2$, —(C=O)R', —SR', —SOR', —$SO_2R$, —N(C=O) OR',—NHR', and —NR'R" wherein each R' and R" independently represents a linear or branched $C_{1-6}$-alkyl group;

the process comprising the reaction between a compound of formula (VI):

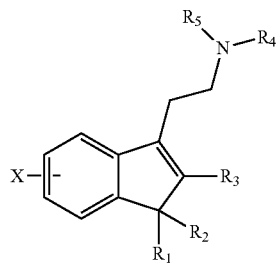

(VI)

wherein X is a halogen;

$R_2$ and $R_3$ are independently selected from hydrogen and a branched or unbranched, saturated or unsaturated, $C_{1-10}$ aliphatic radical, wherein the aliphatic radical may be optionally substituted by one or more substituents selected from the group consisting of a $C_{1-6}$ alkyl group, a $C_{3-9}$ cycloalkyl group, a linear or branched $C_{1-6}$ alkoxy group, —F, —Cl, —I, —Br, —$CF_3$, —$CH_2F$, —$CHF_2$, —CN, —OH, —SH, —$NH_2$, oxo, —(C=O)R', —SR', —SOR', —$SO_2R'$, —NHR', and —NR'R" wherein each R' and R" independently represents a linear or branched $C_{1-6}$-alkyl group, with the proviso that $R_1$ and $R_2$ are always identical; and $R_4$ and $R_5$ together with the bridging nitrogen form a $C_{3-9}$ heterocycloalkyl, optionally having at least one additional heteroatom as a ring member and optionally substituted by a branched or unbranched, saturated or unsaturated $C_{1-10}$ aliphatic radical or by an aryl group optionally monosubstituted by a $C_{1-6}$ alkyl or a halogen;

and a compound of general formula (V):

(V)

wherein each R independently represents a hydrogen or a $C_{1-6}$ alkyl or both R groups together with the bridging boron form a boronic cyclic ester; and $R_6$ is a (5-6)-membered aryl or (5-6)-membered heteroaryl radical optionally substituted by one or more substituents independently selected from the group consisting of a $C_{1-6}$ alkyl group, a linear or branched $C_{1-6}$ alkoxy group, a phenyl group, wherein the phenyl group may be optionally substituted by one or more substituents selected from the group consisting of a $C_{1-6}$ alkyl group, a linear or branched $C_{1-6}$ alkoxy group, —F, —Cl, —I, —Br, —$CF_3$, —$CH_2F$, —$CHF_2$, —CN, —OH, —SH, —$NH_2$, —(C=O)R', —SR', —SOR', —$SO_2R'$, —N(C=O) OR',—NHR', and —NR'R" wherein each R' and R" independently represents a linear or branched $C_{1-6}$-alkyl group, —F, —Cl, —I, —Br, —$CF_3$, —$CH_2F$, —$CHF_2$, —CN, —OH, —SH, —$NH_2$, —(C=O)R', —SR', —SOR', —$SO_2R'$, —N(C=O) OR',—NHR', and —NR'R" wherein each R' and R" independently represents a linear or branched $C_{1-6}$-alkyl group;

in the presence of a base in an inert solvent.

* * * * *

UNITED STATES PATENT AND TRADEMARK OFFICE
CERTIFICATE OF CORRECTION

PATENT NO.        : 9,493,434 B2
APPLICATION NO.   : 14/412021
DATED             : November 15, 2016
INVENTOR(S)       : Alcalde-Pais et al.

It is certified that error appears in the above-identified patent and that said Letters Patent is hereby corrected as shown below:

On the Title Page

Page 2, item (56), Column 1, Line 20 in reference HARUKUNI: "882" should be --982--.

In the Claims

Column 53, Line 46: "Yl)pethyl" should be --yl)ethyl--.

Column 53, Line 52: "pethyl" should be --ethyl--.

Column 53, Line 58: "pethyl" should be --ethyl--.

Column 53, Line 60: "pethyl" should be --ethyl--.

Column 53, Line 62: "pethyl" should be --ethyl--.

Column 53, Line 65: "pethyl" should be --ethyl--.

Column 54, Line 8: "pethyl" should be --ethyl--.

Column 54, Line 12: "pethyl" should be --ethyl--.

Column 54, Line 32: "pethyl" should be --ethyl--.

Column 55, Line 55: "C1alkyl" should be --C1-6alkyl--.

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*